(12) United States Patent
Lympouridis et al.

(10) Patent No.: US 11,073,900 B2
(45) Date of Patent: Jul. 27, 2021

(54) TECHNIQUES FOR MONITORING AND DETECTING RESPIRATION

(71) Applicant: AppliedVR., Inc., Los Angeles, CA (US)

(72) Inventors: Vangelis Lympouridis, West Hollywood, CA (US); Josh Sackman, Studio City, CA (US); Eric Espinoza, Montebello, CA (US); Aaron Robin, Los Angeles, CA (US); Jonathan Graves, Los Angeles, CA (US)

(73) Assignee: AppliedVR., Inc., Los Angeles, CA (US)

(*) Notice: Subject to any disclaimer, the term of this patent is extended or adjusted under 35 U.S.C. 154(b) by 0 days.

(21) Appl. No.: 16/690,900

(22) Filed: Nov. 21, 2019

(65) Prior Publication Data

US 2020/0401211 A1 Dec. 24, 2020

Related U.S. Application Data

(60) Provisional application No. 62/865,910, filed on Jun. 24, 2019.

(51) Int. Cl.
*G06F 3/01* (2006.01)
*G06F 3/16* (2006.01)
(Continued)

(52) U.S. Cl.
CPC ............ *G06F 3/011* (2013.01); *A61B 5/0022* (2013.01); *A61B 5/0816* (2013.01); *A61B 5/486* (2013.01);
(Continued)

(58) Field of Classification Search
CPC ..... G10L 21/0316; G10L 25/51; G10L 25/18; G06F 3/16; G06F 3/011; G06F 3/165; G06F 2203/011; A61B 5/486; A61B 5/6814; A61B 5/0022; A61B 5/6803; A61B 5/0816; A61B 5/681; A61B 5/0205; G02B 27/0176
See application file for complete search history.

(56) References Cited

U.S. PATENT DOCUMENTS

| 2018/0173308 A1 | 6/2018 | Smith | |
| 2018/0256440 A1* | 9/2018 | Francois | ............ A61N 1/36031 |
| 2020/0383581 A1* | 12/2020 | Su | ............ G10L 25/51 |

* cited by examiner

*Primary Examiner* — Yaron Cohen
(74) *Attorney, Agent, or Firm* — Adam P. Daniels, Esq.; Polsinelli LLP

(57) ABSTRACT

A device for monitoring respiration by a user determines whether sound represented by audio data corresponds to an exhalation. For example, the device receives audio data representing sound, determines a frequency spectrum for the audio data (e.g., amplitude distributions of one or more frequencies, etc.), and identifies various frequency bands of interest. Here, the device identifies a first frequency band corresponding to respiration, a second frequency band corresponding to noise, and a third frequency band corresponding to voice harmonics. The device applies a gain to the first frequency band to create an amplified first frequency band, filters or nulls the second frequency band, and inverts the third frequency band to create an inverted third frequency band. The device determines the frequency spectrum corresponds to an exhalation based on a slope value over the amplitude distributions of the amplified first frequency band and the inverted third frequency band.

20 Claims, 14 Drawing Sheets

(51) Int. Cl.
  *G10L 21/0316* (2013.01)
  *G10L 25/18* (2013.01)
  *G10L 25/51* (2013.01)
  *A61B 5/00* (2006.01)
  *A61B 5/08* (2006.01)
  *A61B 5/0205* (2006.01)
(52) U.S. Cl.
  CPC .......... *A61B 5/6803* (2013.01); *A61B 5/6814* (2013.01); *G06F 3/16* (2013.01); *G10L 21/0316* (2013.01); *G10L 25/18* (2013.01); *G10L 25/51* (2013.01); *A61B 5/0205* (2013.01); *A61B 5/681* (2013.01)

TECHNIQUES FOR MONITORING AND DETECTING RESPIRATION

CROSS REFERENCE TO RELATED APPLICATIONS

This application claims the benefit of U.S. Provisional Patent Application Ser. No. 62/865,910, entitled "RESPIRATION MONITORING DEVICES, SYSTEMS AND PROCESSES FOR A WEARABLE HEADSET," filed Jun. 24, 2019, the entirety of which is incorporated herein by reference.

TECHNICAL FIELD

The present disclosure generally relates to portable devices, and more specifically to devices that facilitate monitoring user respiration and providing biofeedback data using a headset.

BACKGROUND

Portable devices such as mobile phones, tablets, smart watches, digital headsets (e.g., Virtual Reality (VR) headsets), and the like have become a mainstay in daily life due to advances in consumer technology, including decreased costs, reduced form factors, increased processing power, improved displays and control interfaces, and so on. The readily accessible nature of such portable devices, in turn, provides new opportunities for businesses to interface and interact with consumers. For example, a number of portable devices have sensors (e.g., gyroscopes, accelerometers, cameras, photo detectors, microphones, etc.) that measure physiological and/or biological activity of a user, and interfaces (e.g. visual displays, speakers, haptic feedback hardware, etc.) that provide meaningful data to the user in the form of biofeedback data. Indeed, a variety of industries leverage biofeedback data to improve user experiences and increase user engagement. However, the true value derived from the biofeedback data for a given user is tied to an underlying accuracy of the measured physiological and/or biological activity.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

An element or functionally similar component is indicated with the same reference number.

DESCRIPTION OF EXAMPLE EMBODIMENTS

Overview

Figure 1:
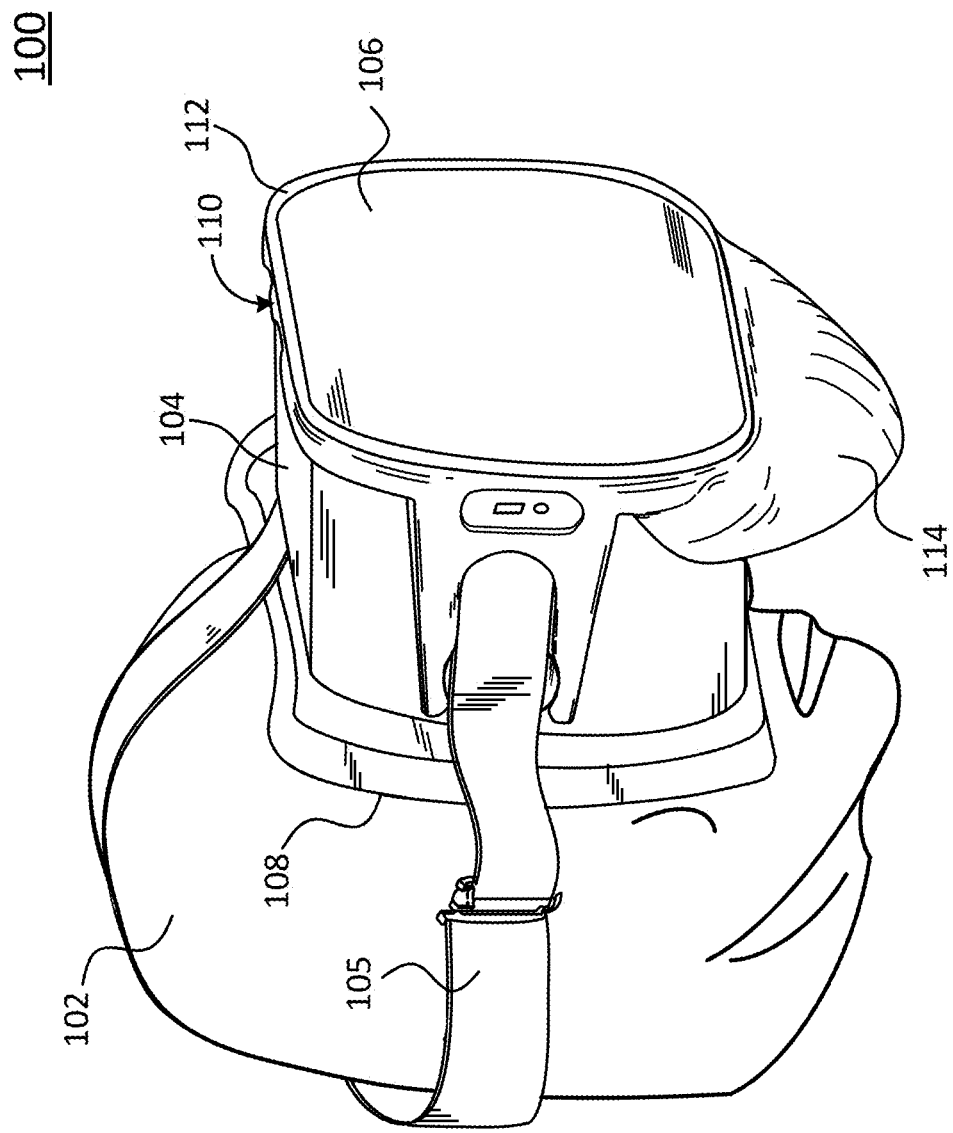
FIG. 1 illustrates a front perspective view of a respiration monitoring system, which includes a respiration guide device coupled to a wearable headset according to one exemplary embodiment of this disclosure.

The present disclosure is directed to improved respiration monitoring techniques that can be used in conjunction with devices (e.g., portable and/or wearable devices) that monitor physiological and/or biological activity of a user and provide biofeedback data representing the same. For example, the present disclosure provides processes and procedures for detecting respiration (e.g., inhalation and/or exhalation) based on audio signals received by devices such as wearable headsets. Notably, these processes and procedures may be employed in conjunction with inventive hardware accessories or configurations that include curved baffles, which help define a partially confined space to generally improve sound signals detected by input interfaces (e.g., microphones) on the device.

In general, the devices include processors that execute instructions corresponding to the disclosed improved respiration monitoring techniques. In one embodiment, the device receives audio data representing sound detected by an input interface (e.g., a microphone). The device further determines a frequency spectrum for the audio data by applying a Fourier Transform to the audio data. The Fourier Transform can include various types of transforms such as a Fast Fourier Transform (FFT), a Discrete Time Fourier Transform (DTFT), and so on. The resultant frequency spectrum of the audio data changes the audio data from a time-domain signal to a frequency domain signal, where the frequency spectrum includes amplitude distributions of the frequencies represented by the audio data. The device further identifies a first frequency band, a second frequency band, and a third frequency band for respective sets of frequencies included in the frequency spectrum. Here, the first frequency band includes a first set of frequencies associated with respiration, the second frequency band includes a second set of frequencies associated with noise, and the third frequency band includes a third set of frequencies associated with human voice. Notably, the device may further identify additional frequency bands and/or sub-sets of frequency bands of interest, as discussed in greater detail herein. The device also applies a gain to the first set of frequencies to create an amplified first frequency band, applies a filter to the second set of frequencies to create a nulled second frequency band, and inverts the third set of frequencies to create a nulled third frequency band. The device further determines that the frequency spectrum corresponds to respiration (e.g., inhalation/exhalation) based on a slope value for the amplitude distributions of the amplified first frequency band and at least a portion of the inverted third frequency band. The slope value can be determined as a mean or an average value between the amplitudes over the frequency spectrum. In some embodiments, the slope value can be calculated as the derivative of the mean or average value. The device further modifies content presented to a user of the device based on detection of an exhalation (e.g., providing visual cues, modifying audio sounds, providing haptic feedback, and so on). Notably, the respiration monitoring techniques generally distinguish between speech or voice and respiration.

In some embodiments, before the device determines the slope value, the device applies a second filter to the third frequency band to isolate specific voice harmonic frequencies in an isolated harmonics band. In these embodiments, the device may also apply a gain to the isolated harmonics band to create an amplified isolated harmonics band. The device determines the frequency spectrum corresponds to respiration based on a slope value over the frequency spectrum, which includes the amplified isolated first frequency band and the amplified isolated harmonics band.

DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

As used herein, the term "portable device(s)" refers to electronic devices able to be easily transported by a user (e.g., a human). Examples of portable devices include, but are not limited to mobile phones, tablets, smart watches, Virtual Reality (VR) headsets, and the like. As used herein, the term "headset" or "wearable headset" refers to a type of portable device that can be worn on a user's head. It is also appreciated that some portable devices (e.g., mobile phones) can be mounted in harnesses worn on a user's head. Thus, in this context, mobile phones may be considered a "headset" or "wearable headset."

As used herein, the term "sound" refers to vibrations that travel through air (or another medium), and includes vibrations corresponding to audible frequencies (e.g., intelligible by a person) as well as non-audible frequencies (e.g., detectable by a computer or electronic device).

As used herein, the terms "front," "back," "rear," "upper," "lower," "right," "left," "top," "bottom," "interior," and "exterior," in this description identify relative spatial relationships between various elements as they are oriented in the figures. It is appreciated that these terms are not meant to limit the element which they describe, as the various elements may be oriented differently in different views and in different applications.

As used herein, the term "coupled" refers to joining two members or components directly or indirectly to one another. Such joining may be stationary in nature or movable in nature and/or such joining may allow for an exchange of electricity, electrical signals, or other types of signals or communication between two members. Such joining may be achieved with the two members only or with the two members and additional intermediate members. Further, such joining may be achieved by integrally forming the two members as a single unitary body or by a physical or electrical connection between the two members (including shared connections with any intermediate members). In this fashion, the joining between two members may be removable, releasable, and/or permanent in nature.

As mentioned above, portable consumer devices are a mainstay in daily life, and provide new opportunities for interfacing and interacting with consumers. Indeed, many portable devices include sensors and interfaces that monitor physiological and/or biological activity, and provide meaningful data in the form of biofeedback.

Biofeedback can improve user experiences and increase user engagement, and has become increasingly prevalent in a variety of industries, including entertainment, gaming, and health and wellness industries (e.g., which can include medical applications). Biofeedback can be passively presented to a user (e.g., displaying user's heart rate) and/or it can be dynamically incorporated into content presented to a user, where the content is adjusted or modified based on physiological/biological activity (e.g., playing a certain song on a playlist based on physical activity). In this fashion, biofeedback can improve a connection between a user and the user's internal biological processes and even create a connection between the user and presented content. Regardless of use-cases and presentment to the user, the true value of biofeedback is tied to the underlying accuracy of measured activity. Accordingly, this disclosure describes devices, systems, and processes that improve monitoring and measuring biofeedback corresponding to respiration of a user.

Referring now to the figures, FIG. 1 illustrates a front perspective view of one exemplary embodiment of a respiration monitoring system 100. As shown, respiration monitoring system 100 includes a headset 104 worn by a user 102, and a respiration guide device 110. Here, respiration guide device 110 is attached or coupled to headset 104. Respiration guide 110 operably includes a curved surface a curved baffle that helps define a partially confined space between a user's mouth and an input interface (e.g., a microphone) on headset 104. This partially confined space facilitates and generally improves the accuracy of the disclosed respiration monitoring techniques.

Headset 104 is a digital device, and can include a virtual reality (VR) device, an augmented reality (AR) device, an enhanced reality (ER) device, and so on. While headset 104 is shown as a particular type of VR device, it is appreciated that headset 104 is representative or any type of wearable headset. For example, in some embodiments, headset 104 may only include a harness for mounting a mobile device or mobile phone of user 102.

Headset 104 includes a front portion 108, a rear portion 106 (e.g., opposite the front portion), and a strap 105 that secures headset 104 to a user's head—e.g., strap 105 shown as a harness worn around the user's head. Front portion 108 interfaces with the head of user 102, and more particularly, a face of user 102. As is appreciated by those skilled in the art, headset 104 includes hardware and software (not shown) for presenting digital content to user 102. For example, the hardware and software can include internal processors, memory, and display interfaces for presenting and creating a VR environment for user 102.

Respiration guide device 110 includes a frame 112 that couples to rear portion 106 of headset 104. As shown, frame 112 surrounds rear portion 106. While frame 112 is shown as surrounding a perimeter of rear portion 106, in some embodiments, frame 112 may only surround a portion of the perimeter of rear portion 106. Respiration guide device 110 also includes wall surface that downwardly depends or extends from frame 112 to form a curved baffle 114. Curved baffle 114 operably directs and/or guides sounds corresponding to a user's respiration (e.g., inhalation and exhalation). Here, curved baffle 114 directs sound toward a bottom portion of frame 112, and thus, toward an input component (not shown) of headset 104. In general, curved baffle 114 forms a curved surface similar to a parabolic reflector, which collects and directs sound toward a focus. Here, the focus of curved baffle 114 corresponds to a position or location of the input component of headset 104 when headset 104 is attached to frame 112. Notably, it is appreciated that while curved baffle 114 is illustrated and described as having specific curvatures, this "curvature" may be also achieved by a number of flat sections disposed at relative angles, where the collective angles of the flat sections form the "curvature" of curved baffle 114.

As illustrated and discussed herein, curved baffle 114 can be symmetrical about a centerline of frame 112 (not shown), but it is also appreciated that such symmetry may be modified depending on the position of the input component of headset 104 relative to source of sound (e.g., a user's mouth). Further, it is also appreciated that the curvature of curved baffle 114 may include multiple curvatures that can be described as spherical, elliptical, and/or parabolic depending on the point of view or cross-section. For example, the curvature of baffle 114 may be described as parabolic when viewed at a horizontal or lateral cross-section, such as the cross-sectional view of FIG. 3C, and/or spherical when viewed at a vertical or longitudinal cross-section, such as the cross-sectional view shown in FIG. 7, as discussed in greater herein.

Figure 2:
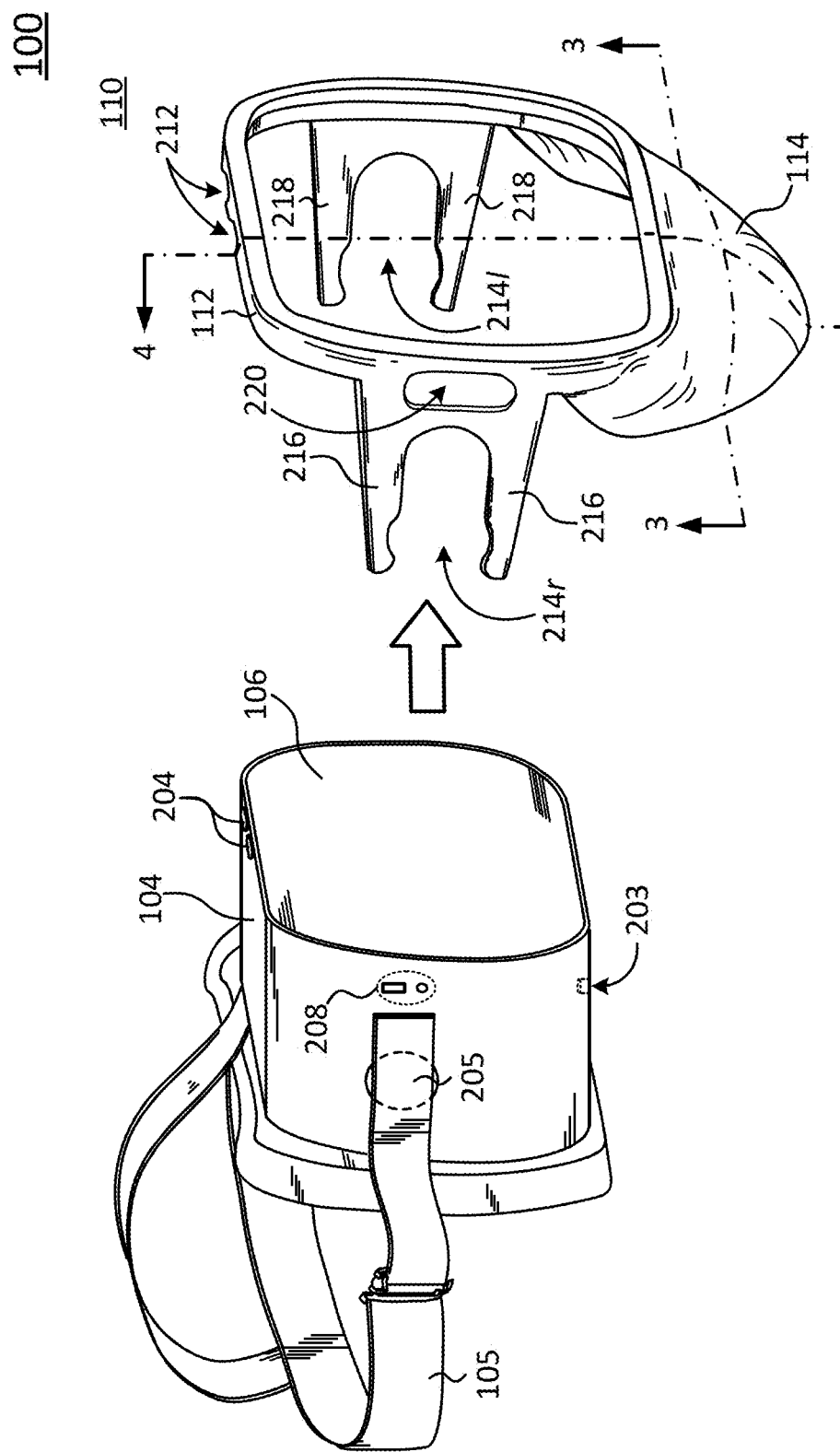
FIG. 2 illustrates an exploded front perspective view of the respiration monitoring system, shown in FIG. 1, showing the respiration guide device detached or decoupled from the wearable headset.

FIG. 2 illustrates an exploded front perspective view of respiration monitoring system 100, showing respiration guide device 110 detached or decoupled from headset 104. In operation—e.g., when attached to headset 104—respiration guide device 110 directs sound using curved baffle 114 toward an input component (e.g., input interface) 203 on wearable headset 104.

Respiration guide device 110 releasably couples to headset 104 based, in part, on the dimensions of frame 112. Frame 112 defines a frame perimeter dimensioned to surround (at least a portion of) a perimeter of headset 104 when attached to headset 104 to couple or attach frame 112 to rear portion 106 of headset 104. In this fashion, the frame perimeter surrounds the perimeter of headset 104 when coupled to headset 104. Here, the frame perimeter surrounds a corresponding perimeter of headset 104, however, in some embodiments, it is appreciated that the frame perimeter may only surround a portion of the perimeter of headset 104.

Referring to input component 203, this component represents electronic interfaces that operably measure or detect vibrations corresponding to the sound of respired air (e.g., inhalation, exhalation, etc.). For example, input component 203 can include electronic interfaces such as voice coils, diaphragms, drivers, and other components such as those found in microphones and speakers. As shown, input component 203 is internally disposed within an interior of headset 104, however it is appreciated that input component 203 may be positioned in a plurality of other locations about or within headset 104 and/or external to headset 104 (e.g., in or on respiration guide device 110).

Input component 203 receives the sound directed by curved baffle 114 and transforms the sound into corresponding electrical signals, as is appreciated by those skilled in the art. As one example, input component 203 can include a diaphragm that vibrates or resonates at a frequency corresponding to the received sound. The diaphragm's movement can move a voice coil through a magnetic field, which creates an electrical current (e.g., electrical signals). As is appreciated by those skilled in the art, the electrical signals are further processed by a processor to measure and generate biofeedback metrics corresponding to the sound, and thus, the respiration of user 102.

Notably, the biofeedback metrics can include, for example, amplitudes, rates, volumes, etc. In some embodiments, the biofeedback metrics can be used by applications executing on headset 104 to improve user experiences and increase user engagement. For example, the biofeedback metrics may be used to adjust content presented to the user. Here, graphical elements may be generated and presented to the user. These graphical elements can include representations of the respiration metrics, including for example, numbers corresponding to a respiration rate, visualizations corresponding to virtually respired air (e.g., similar to condensation from an exhale on a cold day), and so on. In addition, the biofeedback metrics may adjust the content itself—e.g., increase or decrease the volume or speed of audio content, change color pallets to reflect faster or slower respiration rates, etc.

FIG. 2 also shows one or more control buttons 204 positioned on a top side of headset 104, and one or more ports 208 positioned on a right side of headset 104. Control buttons 204 represent hardware components (e.g., switches, dials, buttons, etc.) for controlling various aspects of headset 104, including for example, power, volume, selection, and so on. Ports 208 represent interface components that allow a user to couple other electronic devices to headset 104. For example, ports 208 can include auxiliary ports, headphone ports, universal serial buses (USB), and so on. It is appreciated that the illustrated control buttons and ports are representative of any type of input interface and/or control interface to headset 104, and further, other types of headsets may include additional or fewer buttons and/or ports as appropriate.

Notably, frame 112 also defines one or more grooves 212 and an aperture 220 that permits access to control buttons 204 and ports 208, respectively. In particular, aperture 220 defines an open space that permits access there-through to ports 208 (e.g., in the coupled or attached state). Similarly, grooves 212 permit access to control buttons 204 (e.g., when frame 112 is attached or coupled to headset 104).

Respiration guide device 110 also includes one or more attachment flanges such as flanges 216 and flanges 218. Here, flanges 216 and flanges 218 are disposed on frame 112 to form attachment mechanisms that releasably secure respiration guide device 110 to headset 104. In particular, flanges 216 and flanges 218 define respective U-shaped cut-outs indicated by reference numbers 214r (right side) and 214l (left side). These U-shaped cut-outs operably receive corresponding portions of headset 104 while flanges 216 and flanges 218 releasably couple to the corresponding portions of headset 104. For example, strap 105 is attached to headset 104 by a fastener or harness mount 205. When respiration guide device 110 is attached to headset 104, cut-outs 214r and 214l receive respective harness mounts 205. Flanges 216 and 218 clip or attach to respective harness mount(s) 205 to releasably secure frame 112 to headset 104.

Cut-outs 214r and 214l are shown in a particular size and configuration for a specific headset (e.g., headset 104); however it is appreciated that the shape of the cut-outs and the corresponding flanges may be readily modified to fit other types of headsets. Moreover, while the attachment mechanisms formed by flanges 216 and 218 include two pairs of flanges on either side of frame 112, it is appreciated a single pair of flanges may be employed. In addition, or in the alternative, a variety of other attachment mechanisms may also be employed and/or substituted for the pairs of flanges (e.g., friction fit attachments, adhesives, clasps, threaded attachments, a single attachment flange, multiple pairs of attachment flanges, etc.). In other embodiments, flanges 216 and 218 are optional, since the frame perimeter may form a friction fit seal about the perimeter of headset 104 in order to releasably secure frame 112 to headset 104.

Figure 3A:
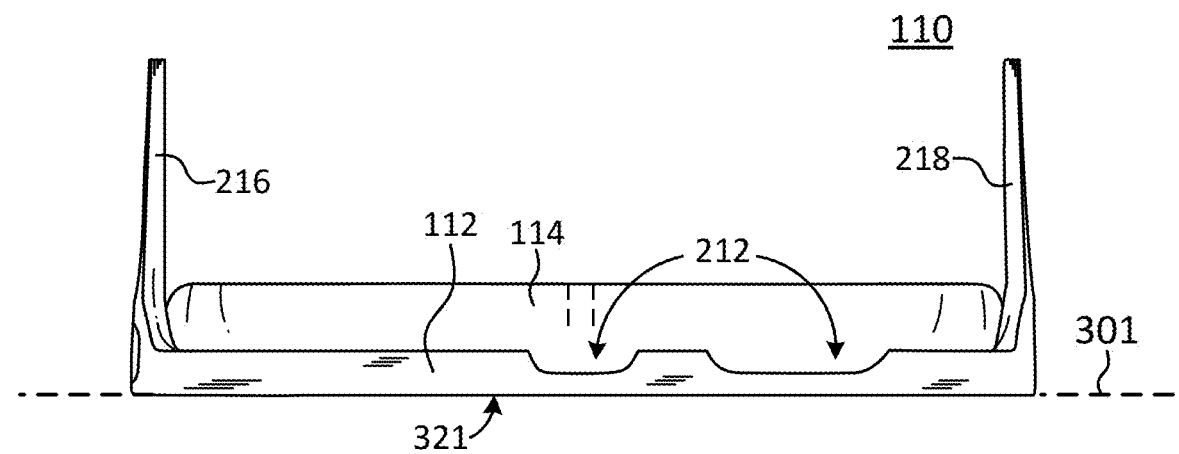
FIG. 3A illustrates a top side plan view of the respiration guide device shown in FIG. 1.
Figure 3B:
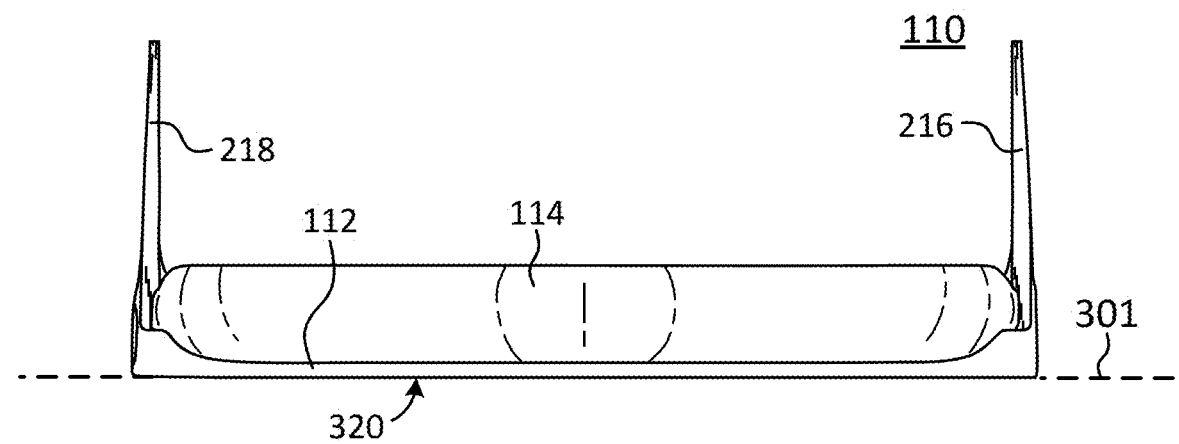
FIG. 3B illustrates a bottom side plan view of the respiration guide device shown in FIG. 1.
Figure 3C:
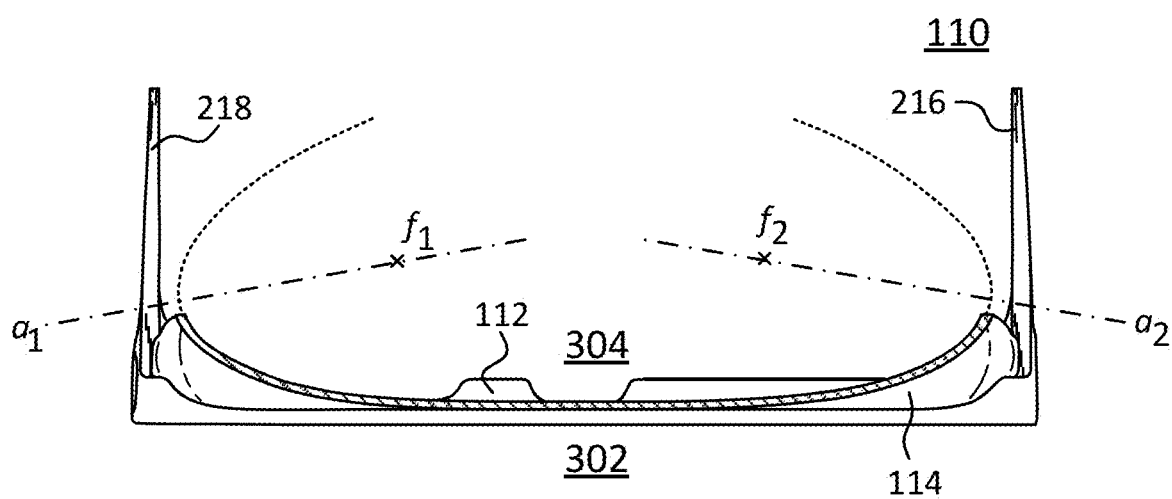
FIG. 3C illustrates a partial cross-sectional bottom side plan view of the respiration guide device, viewed at cut lines 3-3 shown in FIG. 2.

Referring to FIGS. 3A-3C, FIG. 3A illustrates a top side plan view of respiration guide device 110, FIG. 3B illustrates a bottom side plan view of respiration guide device 110, and FIG. 3C illustrates a cross-section side plan view of respiration guide device 110, viewed from cut lines 3-3 shown in FIG. 2.

FIG. 3A illustrates grooves 212 defined along a top portion 321 of frame 112. As discussed, grooves 212 permit access to control buttons (e.g., control buttons 204) when respiration guide device 110 is attached to headset 104, and it is appreciated that these grooves may modified to appropriate shapes and sizes depending on the type of headset and placement of control buttons (if any).

FIG. 3B illustrates the bottom side plan view of respiration guide device showing a bottom portion 320 (opposite top portion 321 shown in FIG. 3A). FIGS. 3A and 3B both illustrate a frame plane 301 defined by an exterior perimeter of frame 112. As shown, frame plane 301 is represented as a dash line in the cross-sectional views of FIGS. 3A and 3B. Notably, flanges 216 and 218 extend or protrude from frame 112 at an angle substantially orthogonal to frame plane 301.

FIG. 3C illustrates a cross-sectional side plan view of respiration guide device 110 viewed along cut-lines 3-3 of FIG. 2. As discussed, curved baffle 114 may be constructed of a variety of different shapes and/or sizes to focus, guide, and/or otherwise create a partially confined space for directing sound from user 102 toward a desired focal point—here, a bottom portion of frame 112, which is proximate to input component 203 when frame 112 is coupled or attached to headset 104.

The cross-sectional view illustrated in FIG. 3C is a horizontal or lateral cross-sectional view of respiration guide device 110. This cross-sectional view shows generally parabolic curvatures of curved baffle 114. For reference and discussion of these curvatures, FIG. 3C includes reference numbers 302 and 304, where reference number 302 refers to an exterior side of respiration guide device 110 and reference number 304 refers to an interior side of respiration guide device 110, opposite the exterior side. "Interior side" and "exterior side" are relative terms, where the interior side refers to the inside of respiration guide device 110 (e.g., proximate to a user's face) when frame 112 is attached to headset 104, and the exterior side refers to the outside of respiration guide device 110 (e.g., distal or facing away from the user's face) when frame 112 is attached to headset 104.

As shown, the curvature of curved baffle 114 is represented by two parabolas, having respective foci, f1, f2, and respective axes of symmetry, a1 and a2. Here, curved baffle 114 may be symmetrical about a centerline of frame 112 (not shown), such that the shape of curved baffle 114 on one side of the centerline is a mirror image of the shape of curved baffle on the other side of the centerline. Further, the curvature on either side of the centerline of frame 112 includes additional respective symmetries. For example, the parabola indicated by focus f1 is symmetrical about axis of symmetry a1, and the parabola indicated by focus f2 is symmetrical about axis of symmetry a2. With respect to interior side 304 and exterior side 302, curved baffle 114 curves away from exterior side 302 toward interior side 304 at the lateral cross-section shown in FIG. 3C.

In some embodiments, the respective axis of symmetry may be offset relative to each other to form an overall non-symmetrical curvature of curved baffle 114 (e.g., non-symmetrical as compared to the centerline of frame 112). Further, it is appreciated that the curvature indicated by two parabolas in this cross-sectional view is not limited to parabolic shapes, but may include any suitable shape (e.g., elliptical, circular, non-geometric shapes, etc.) for directing sound corresponding to respired air toward a portion of frame 112 and/or a portion of headset 104 (e.g., when attached to the headset).

In addition, curved baffle 114 includes a substantially smooth shape, however it is appreciated that curved baffle 114 may include interior ridges, ribs, and/or compartments that create partitions for segregating portions of air and/or sound corresponding to respired air. These partitions can provide additional structural integrity for curved baffle 114 and/or direct, amplify, or attenuate the sound corresponding to respired air as appropriate.

Further, while FIG. 3C illustrates the wall forming curved baffle 114 having specific cross-sectional area and shape, it is appreciated that curved baffle may have a thinner, thicker, and/or non-uniform cross sectional areas that provide proper structure and shape for directing the sound toward a particular focus or position. Moreover, baffle 114 may be constructed of any suitable material to achieve the above, such as, but not limited to, acrylonitrile butadiene styrene (ABS) plastic, polyurethane, thermoplastic polymers, other plastics, rubber, wood, metals, etc. Further, although FIG. 3C illustrates baffle 114 as solid, baffle 114 may also be constructed to be porous, hollow, or of any other suitable density.

Figure 4:
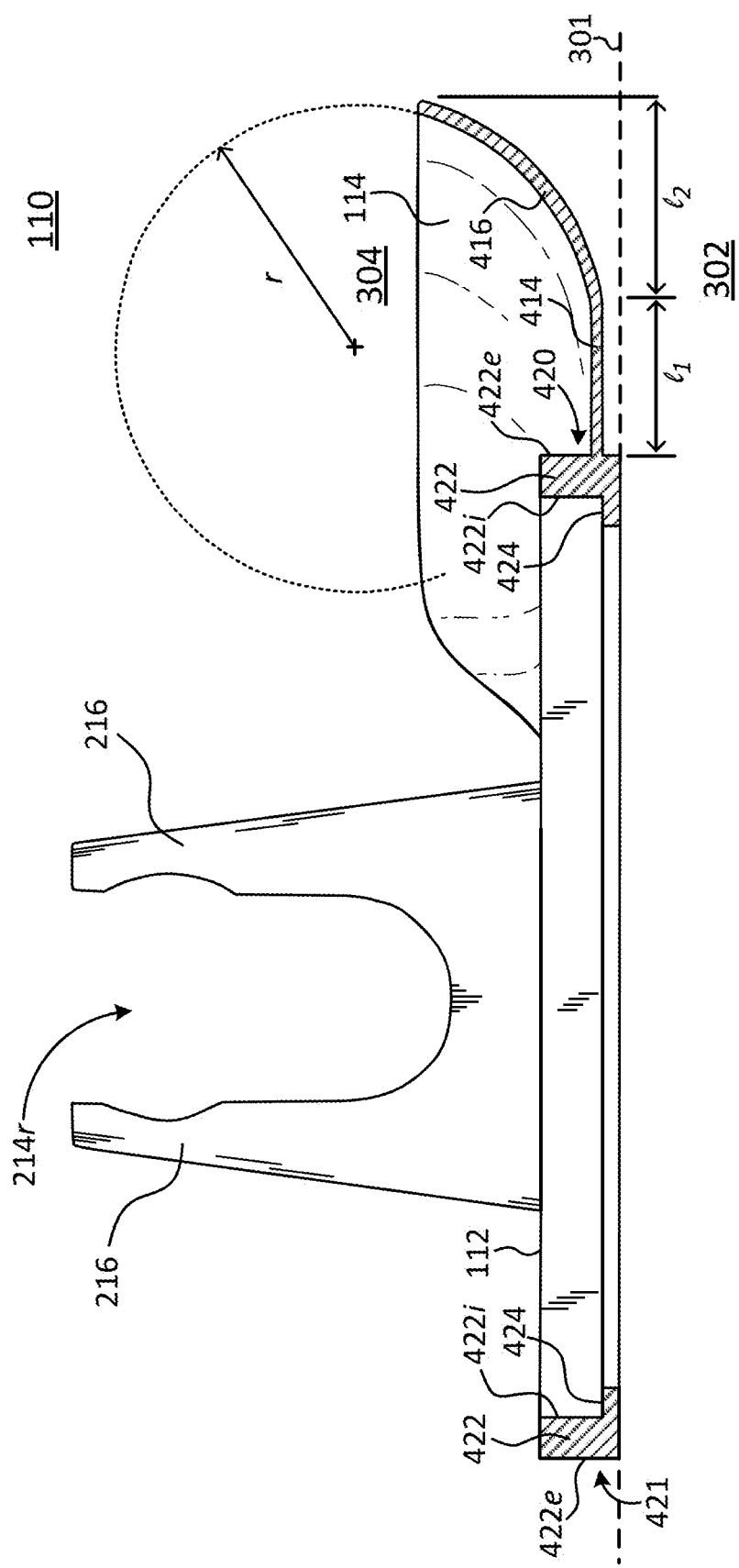
FIG. 4 illustrates a cross-sectional side elevation view of the respiration guide device, viewed at cut lines 4-4 shown in FIG. 2.

FIG. 4 illustrates a cross-sectional side elevation view of respiration guide device 110 shown in FIG. 2, viewed from cut lines 4-4. As shown, frame 112 includes a number of integrally formed components, including a skirt 424, a sidewall 422 having an interior edge 422i and an exterior edge 422e, and curved baffle 114. It is appreciated that the illustrated components may be separately formed and further, may be made of different materials with varying densities.

Curved baffle 114 is formed by a wall surface that downwardly depends from a bottom portion 420 (opposite a top portion 421) of frame 112. As mentioned, curved baffle 114 has a generally parabolic curvature for collecting and directing respired air toward a focus—e.g., input component 203 of headset 104. As is appreciated by those skilled in the art, the parabolic curvature of curved baffle 114 may be modified based on the relative position of input component 203 (e.g., when respiration guide device 110 is coupled to headset 104). In addition, it is appreciated that curved baffle 114 can have elliptical, spherical, and/or asymmetrical curvatures. In general, the size, shape, and curvature of curved baffle 114 optimally creates a partially confined space for directing respired air toward input interface 203 of headset 104 (not shown here). Accordingly, the curvature is based on the location of input component 203 on headset 104 and the source of respired air (e.g., a user's mouth). At the same time however, it is also appreciated that relative improvements in directing the respired air from various types of curvatures may be balanced against aesthetics (e.g., look, appeal, consumer preferences, etc.).

Sidewall 422 defines a frame perimeter that substantially surrounds a corresponding perimeter of a housing of headset 104 (or a portion thereof). For example, the frame perimeter defined by sidewall 422 surrounds the perimeter of rear portion 106 of headset 104 when respiration guide device 110 is attached or coupled to headset 104. Importantly, sidewall 422 and skirt 424 facilitate a releasable coupling between respiration guide device 110 and headset 104.

Skirt 424 is a recessed skirt that forms a shoulder with sidewall 422. The shoulder particularly abuts interior edge 422i of sidewall 422. In operation, frame 112 is releasably coupled to a headset—e.g., headset 104—such that a portion of the housing of the headset rests in interior recessed skirt 424 and on the shoulder (e.g., interior edge 422i). As discussed, frame 112 may be specifically sized such that recessed skirt 424 and interior edge 422i form a friction fit attachment mechanism to releasably couple frame 112 to the headset without requiring additional flanges (e.g., flanges 216/218). Here, the shoulder formed between interior edge 422i and skirt 424 is a circumferential shoulder about the interior perimeter of frame 112. In some embodiments, it is appreciated that the friction fit can provide sufficient force to secure frame 112 to headset 104 without requiring additional attachment mechanisms formed by flanges 216 and 218.

The shoulder formed between skirt 424 and interior edge 422i also operably forms a seal between frame 112 and a headset, which creates a partially confined space between curved baffle 114 and exterior edge 422e. In this fashion, skirt 424 and the shoulder formed with interior edge 422i define a socket that receives a rear portion of the headset (e.g., rear portion 106 of headset 104). Interior edge 422i defines the shape of the socket and skirt 424 defines a "bottom" of the socket. That is, the position and depth of the shoulder formed by skirt 424 and interior edge 422i determine the position of frame 112 relative to the headset (when attached). Typically, the depth of the shoulder is relatively shallow such that frame 112 is positioned proximate to a rear portion of the headset.

In some embodiments, however, frame 112 does not include a skirt 424. In these embodiments, interior edge 422i (only) couples to the housing of the headset and forms the seal between frame 112 and the headset. In these embodiments, frame 112 may be positioned along various portions of the housing of the headset (e.g., since there is no "bottom" of the socket).

Further, while curved baffle 114 forms a shoulder with exterior edge 422e, in some embodiments, curved baffle 114 may not form such a shoulder. In these embodiments, curved baffle 114 may be formed with the same thickness as sidewall 422 and/or formed with a smooth tapering thickness from sidewall 422, which transitions in curved baffle 114.

With respect to the confined space between curved baffle 114 and exterior edge 422e, this shape is defined by the curvature of curved baffle 114. As discussed, this shape is selected to efficiently direct sound toward a specific portion of frame 112 (e.g., bottom portion 420), and thus, toward a specific portion of the headset when frame 112 is attached to the same. As discussed, the headset shown in the figures of this application includes an input component or an input interface (e.g., input component 203) that is located proximate to bottom portion 420 of frame 112 attached to the headset. In this fashion, curved baffle 114 directs sound corresponding to respired air toward a bottom portion 420 of frame 112, and thus, toward the input component of the headset. The input component 203 of the headset operably detects and measures sounds to determine breathing metrics of the user in accordance with the respiration monitoring techniques discussed herein.

Still referring to FIG. 4, to curved baffle 114 is formed by a wall surface or wall portion 414 that downwardly depends from bottom portion 420 of frame 112. This wall portion 414 forms a curved portion 416 of curved baffle 114. Here, wall portion 414 extends from bottom portion 420 by a first length $l_1$, while curved portion 416 extends from wall portion 414 by a second length $l_2$. Collectively, wall portion 414 and curved portion 416 form curved baffle 114. Notably, in some embodiments, curved baffle 114 may include multiple curvatures where, for example, wall portion 414 has a curvature different than that of curved portion 416.

As mentioned, curved baffle 114 may include multiple curvatures, depending on the viewpoint (e.g., FIG. 3C illustrates parabolic curvatures). As shown FIG. 4, the curvatures of curved baffle 114 may also include a circular or elliptical cross-sectional shape indicated by radius r. In general, the curvature of curved baffle 114 is shaped and dimensioned for creating a partially confined space that optimizes directing sound corresponding to respiration toward a particular location. Here, that location corresponds to the position of an input component of the headset when attached to frame 112.

Figure 5:
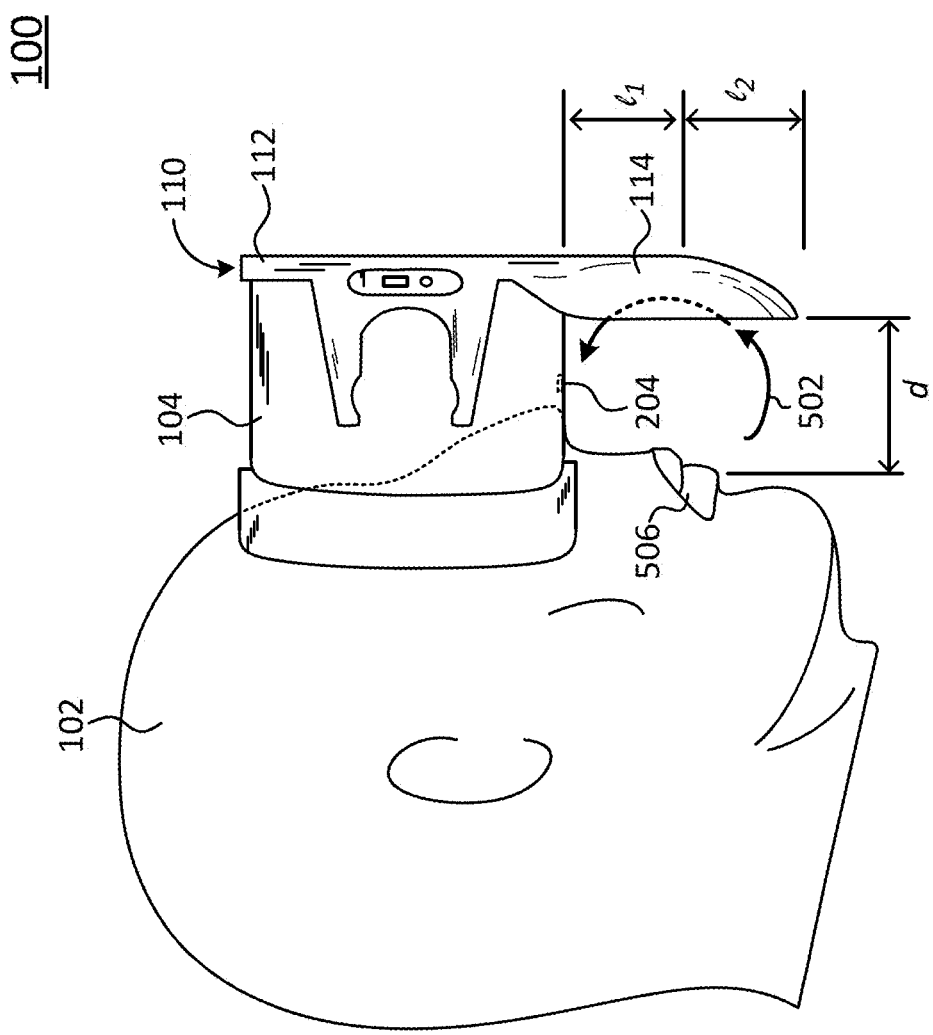
FIG. 5 illustrates a right side elevation view of the respiration guide device shown in FIG. 1, further showing the respiration guide device directing respired or exhaled air from a user toward an input component on the wearable headset.

FIG. 5 illustrates operations for directing sound by curved baffle 114 toward input component 203 on headset 104. In particular, FIG. 5 illustrates a right side elevation view of respiration monitoring system 100. As shown, curved baffle 114 creates a partially confined space that directs sound, including respired air 502, from user 102 toward input component 203. Notably, respired air 502 can include exhaled air or inhaled air.

As shown, frame 112 includes a wall surface that downwardly depends or extends from frame 112 to form curved baffle 114. Preferably, the wall surface and curved baffle 114 are integrally formed, but, it also appreciated that the curved baffle and wall surface components may be separately formed.

Dimensions of curved baffle 114 are indicated by a length $l_1$ and a length $l_2$. Length $l_1$ and a length $l_2$ represent a total length of curved baffle 114 extending extends from a bottom portion of frame 112. In the side-elevation view shown, length $l_1$ represents a length of a downwardly extending first portion of curved baffle 114 (e.g., the downwardly depending wall surface) and length $l_2$ represents a second portion of curved baffle 114 having a curvature defined by a radius (e.g., ref. FIG. 4).

In operation, respiration guide device 110 is positioned relative to headset 104 such that curved baffle 114 is at a distance d relative to a mouth 506 of user 102 (e.g., a source of the sound corresponding to the respired air). Distance d represents to an optimal distance from mouth 506 to curved baffle 114 for facilitating operations by curved baffle 114 to direct sound corresponding to respired air 502. Distance d is determined as a function of a sensitivity of input component 203, a shape and size of the wall surface/curved baffle 114, a curvature of curved baffle 114, and a shape and size of headset 104. It is appreciated that different headsets can vary in size or shape, which may result in different distances d. Thus, distance d may be adjusted or varied in order to accommodate differently headsets.

Exhaled air 502 from the user's mouth 506 and traverses distance d toward curved baffle 114. Curved baffle 114 directs the sound corresponding to respired air 502 along its curved interior, along lengths $l_1$ and $l_2$ towards a bottom portion of frame 112 (labeled with reference number 420 in FIG. 4). As mentioned, frame 112 forms a seal, at least in part, about headset 104. This seal helps further direct the sound corresponding to respired air 502 from the bottom portion of frame 112 toward input component 203.

Any combination and variation of distance d, length $l_1$, length $l_2$, and/or radius $r_1$ can be used to the sound corresponding to respired air from the user's mouth 506 toward input component 504. In some embodiments, curved baffle 114 may adjustable such that it can be positioned at varying optimal distances d relative to the user's mouth 506.

Figure 6:
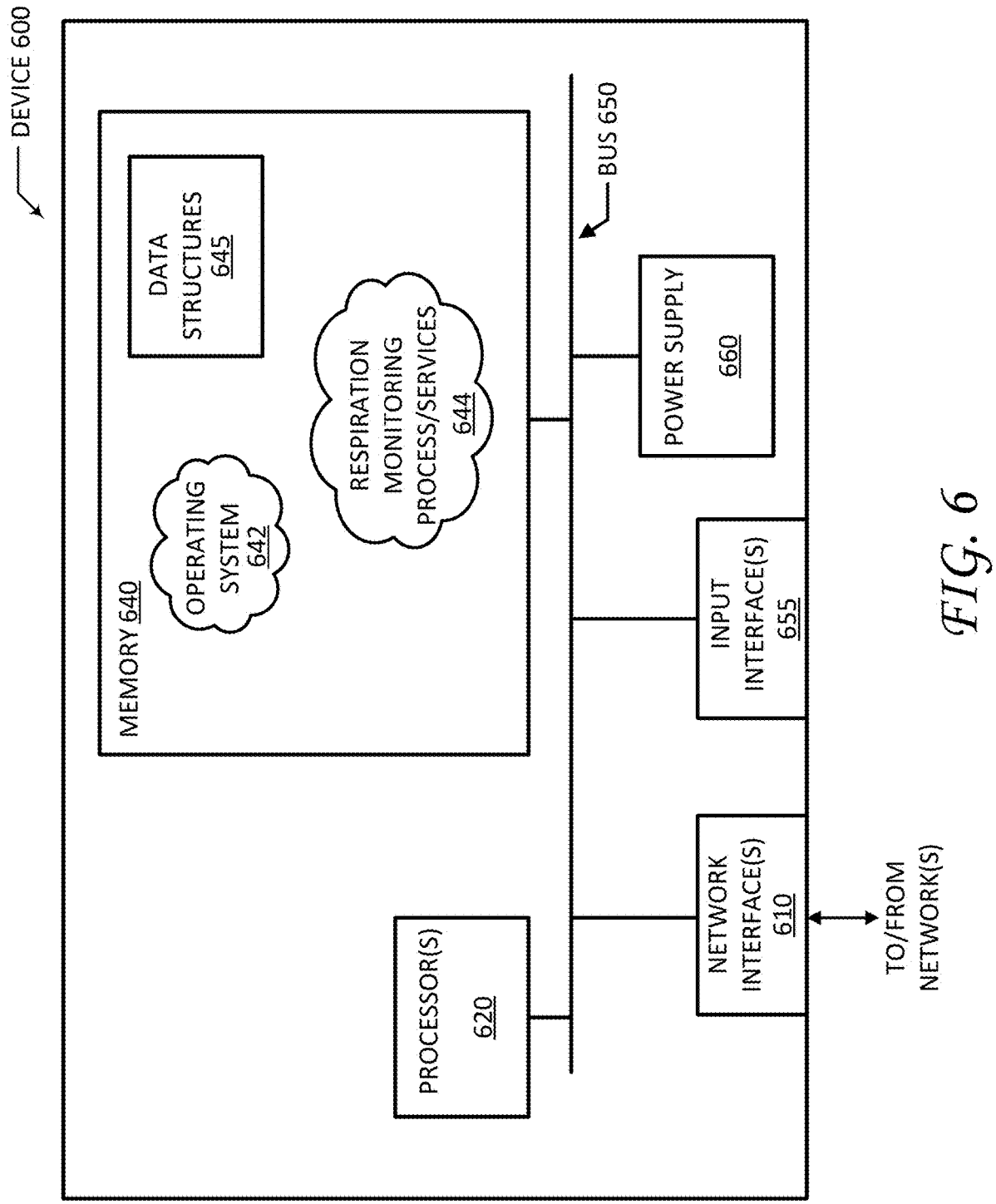
FIG. 6 illustrates a schematic block diagram of an exemplary respiration monitoring device, such as a headset device, according to one or more examples of this disclosure.

FIG. 6 illustrates a schematic block diagram of an exemplary device 600 that may be used with one or more examples described herein. For example, device 600 can represent components of respiration monitoring system 100, such as headset 104 shown in FIG. 1.

Alternatively, it is also appreciated that one or more components of device 600 may be incorporated into a larger distributed computing environment, as is appreciated by those skilled in the art. For example, in a distributed computing environment, the individual components of device 600 may represent logical or virtual components, where such components are implemented and hosted by a data center (e.g., using servers, distributed memory, communication links/networks, software modules, services, objects, distributed data structures, and so on).

However, for purposes of discussion herein, reference is made to a headset example, where device 600 represents headset 104. As shown, the illustrative device 600 comprises one or more network interfaces 610, at least one processor 620, a memory 640 interconnected by a system bus 650, input interfaces 655, which may correspond to input component(s) 203 (e.g., a microphone) shown in FIG. 2, and a power supply 660 (e.g., battery, plug-in, etc.).

Network interface(s) 610 contain the mechanical, electrical, and signaling circuitry for communicating data over links (e.g., wires or wireless links) within a network (e.g., the Internet). Network interfaces 610 may be configured to transmit and/or receive data using a variety of different communication protocols, as will be understood by those skilled in the art.

Memory 640 comprises a plurality of storage locations that are addressable by processor 620 for storing software programs and data structures associated with the examples described herein. Processor 620 may comprise necessary elements or logic adapted to execute the software programs and manipulate data structures 645. An operating system 642, portions of which are typically resident in memory 640 and executed by processor 620, functionally organizes the device by, inter alia, invoking operations in support of services and/or software processes executing on the device. These services and/or software processes may comprise an illustrative "respiration monitoring" process/service 644. Note that while respiration monitoring processes/services 644 are shown in centralized memory 640, as mentioned, these processes or services can be implemented in a distributed communication environment (e.g., a cloud-based data center, etc.).

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, while the processes have been shown separately, those skilled in the art will appreciate that processes may be routines or modules within other processes.

For example, processor 620 can include one or more programmable processors, e.g., microprocessors or microcontrollers, or fixed-logic processors. In the case of a programmable processor, any associated memory, e.g., memory 640, may be any type of tangible processor readable memory, e.g., random access, read-only, etc., that is encoded with or stores instructions that can implement program modules, e.g., a module having process 644 encoded thereon. Processor 620 can also include a fixed-logic processing device, such as an application specific integrated circuit (ASIC) or a digital signal processor that is configured with firmware comprised of instructions or logic that can cause the processor to perform the functions described herein. Thus, program modules may be encoded in one or more tangible computer readable storage media for execution, such as with fixed logic or programmable logic, e.g., software/computer instructions executed by a processor, and any processor may be a programmable processor, programmable digital logic, e.g., field programmable gate array, or an ASIC that comprises fixed digital logic, or a combination thereof. In general, any process logic may be embodied in a processor or computer readable medium that is encoded with instructions for execution by the processor that, when executed by the processor, are operable to cause the processor to perform the functions described herein.

Illustratively, respiration monitoring process 644 can perform the respiration monitoring techniques described herein may be performed by hardware, software, and/or firmware, such as in accordance with the, which may contain computer executable instructions executed by processor 620 to perform functions relating to capturing sound, filtering specific frequencies to isolate, as described herein.

As noted above, the value provided by biofeedback data for a given user directly relates to the underlying accuracy of measuring (or monitoring) corresponding physiological/ biological activity. Accordingly, the techniques disclosed herein are directed to improving respiration monitoring with increased accuracy and efficient processes that are compatible with hardware found in devices such as a wearable headset. In general, the disclosed respiration monitoring techniques analyze and process audio signals received by a device (e.g., a wearable headset), detect respiration (e.g., inhalation, exhalation, etc.) based on the audio signals, generate meaningful biofeedback data, and leverage this biofeedback data to enhance, optimize, or otherwise modify user experiences (e.g., adjust content).

For example, in one embodiment, respiration monitoring process 644 incorporates meaningful biofeedback into a digital experience (e.g., Virtual Reality (VR), Augmented Reality (AR), Enhanced Reality (ER), etc.) where the content presented to a user is adjusted based on the detected respiration (e.g., exhalation/inhalation). The content, in this context, can include visual, audio, and/or even haptic feedback. In turn, the respiration monitoring process 644 can modify the digital experiences, which can aid medical applications by controlling or influencing a user's state of mind and/or emotions (e.g., calming a patient down, controlling breathing rates, etc.).

In detail, respiration monitoring process 644 process spectrally analyzes audio data to determine if respiration is present in an audio signal by transforming audio data into a frequency spectrum of amplitude distributions. The respiration monitoring processes further identifies and applies filters and multipliers (e.g., gains) to specific frequency bands, and inverts the amplitudes associated with specific harmonic frequency bands associated with voice. The respiration monitoring process also determines a mean or an average slope value that compares the amplitude distributions between the filtered and inverted frequency bands. This mean or average slope value is compared to a threshold value to determine and distinguish respiration sound (e.g., exhalation) from human speech and/or other environmental sounds. With particular respect to the mean or average slope value, respiration monitoring process 644 can calculate this average slope value based on a derivative of a moving average. In addition, respiration monitoring process 644 can iteratively determine the presence (or absence) of an exhalation for multiple audio signals corresponding to different time periods, which can further identify respiration rates, intensities, and so on. In addition, as mentioned, respiration monitoring process 644 leverages the detected respiration to change or modify a user experience (e.g., when a user is wearing the headset) by adjusting the content presented to the user. By monitoring a user's respiration and incorporating biofeedback into an experience, users can be more aware of how their body responds to stress. And in the context of medical applications, this biofeedback can be used calm users down, control breathing rates, and so on.

Figure 7:
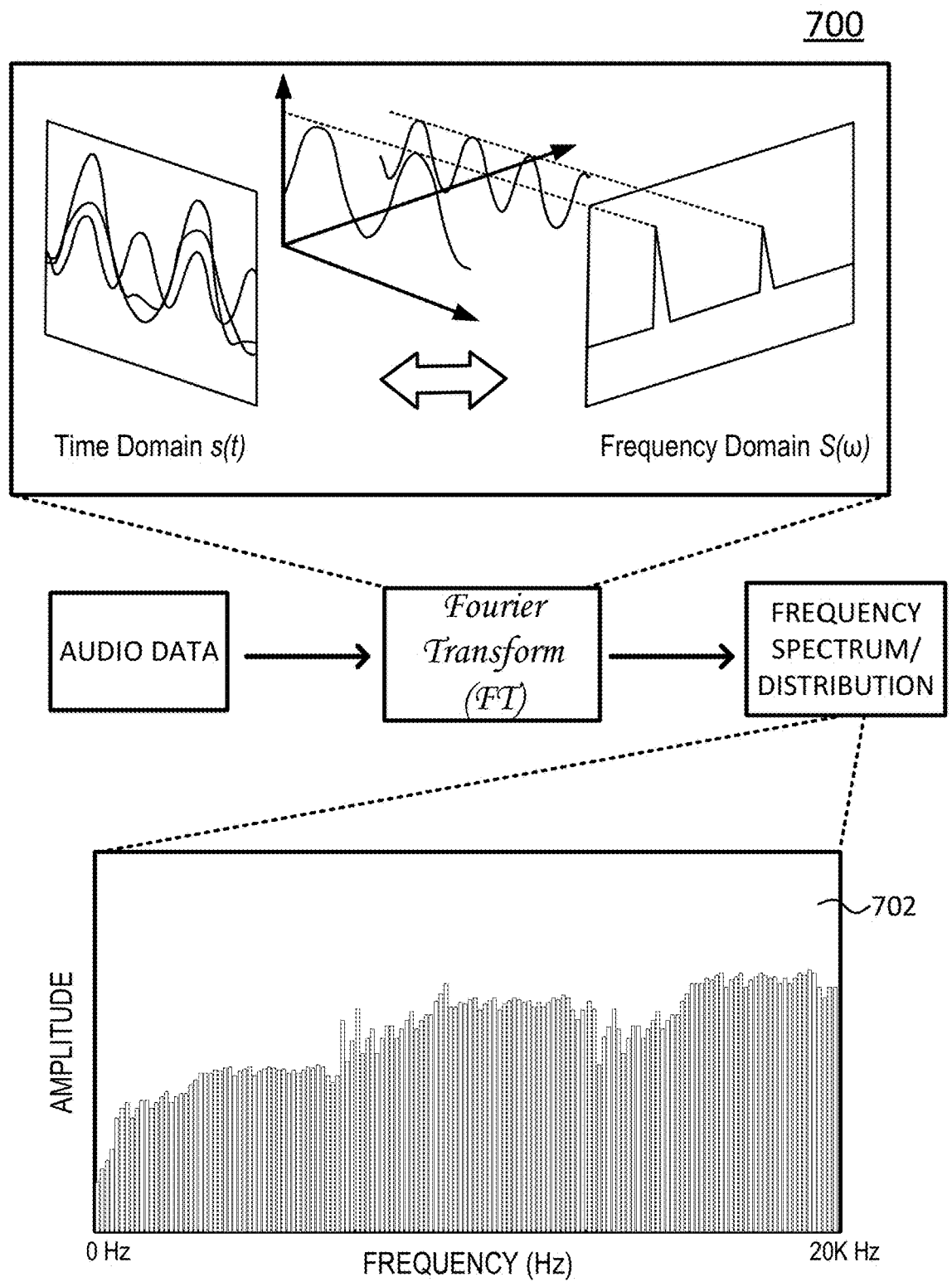
FIG. 7 illustrates a diagram of an exemplary procedure for decomposing an audio signal into its constituent frequencies.

FIG. 7 illustrates a diagram 700, showing an example procedure for decomposing an audio signal into its constituent frequencies. In particular, diagram 700 provides a visual representation that shows how the disclosed respiration monitoring techniques transform audio signals (e.g., audio data) from a time-based function to a frequency-based function. Put differently, diagram 700 illustrates the transformation of audio data from the time domain s(t) into the frequency domain s(ω).

Here, the transformation is achieved by applying a Fourier Transform (FT) to a time-based audio signal or audio data representing the audio signal. The FT function yields a frequency distribution of signal amplitudes, which are shown in graph 702. It is appreciated that various types and iterations of Fourier Transforms exist, and further, the exact Fourier Transform used by the disclosed respiration monitoring techniques may be selected based on the type of data and the context of its underlying application.

For example, in on embodiment, the respiration monitoring techniques use a Fast Fourier Transform (FFT) to compute a Discrete Time Fourier Transform (DTFT or DFT) for a digital audio signal. In operation, the respiration monitoring techniques may be performed by device 600 (e.g., in an embodiment of a wearable headset), and/or as part of the distributed processing environment as discussed above, where for example, device 600 receives and transmits audio data to a cloud-based computing environment for analysis. As discussed below, subsequent analysis, filtering, and respiration determinations are calculated based on manipulating and evaluating audio data, and more specifically, the signal amplitudes for different frequency bands (i.e. ranges of frequencies) in the audio data.

FIGS. 8A-8H collectively illustrate power spectral density graphs 801-808 for an audio signal, showing frequency-domain plots of power per Hz vs. frequency. Graphs 801-808 show various aspects of the disclosed respiration monitoring processes which may be embodied by respiration monitoring process 644 (discussed above). Graphs 801-808 illustrate different processing steps for the disclosed respiration monitoring process. Although the graphs 801-808 are discussed in a particular order herein, this order is provided for purposes of example and discussion, not limitation. It is appreciated that these processing steps are not limited to being performed in this particular order, but instead the processing steps may be performed in any order as appropriate. Further, it is also appreciated that graphs 801-808 are provided to visually represent the various steps of the disclosed respiration monitoring process. In typical operation, this process executes behind on a device (e.g., a wearable headset) and/or in a distributed computing environment where many of these processing steps are not shown to the user. Instead, the user may be presented with the result of this process (e.g., respiration rates, intensities, etc.), and/or the content presented to the user may be otherwise adjusted—e.g., music may be turned down/up, different sounds may be played, visual content may be adjusted, haptic feedback can be provided, and so on.

It should be noted that while specific frequency ranges are illustrated in graphs 801-808 and described herein, these frequency ranges are approximations, and further these frequency ranges may be affected by, for example, different user-specific considerations (e.g., each user may have a unique respiration signature), hardware configurations for different headsets (e.g., where the microphones have different sensitivities, positions, etc.), and so on.

Figure 8A:
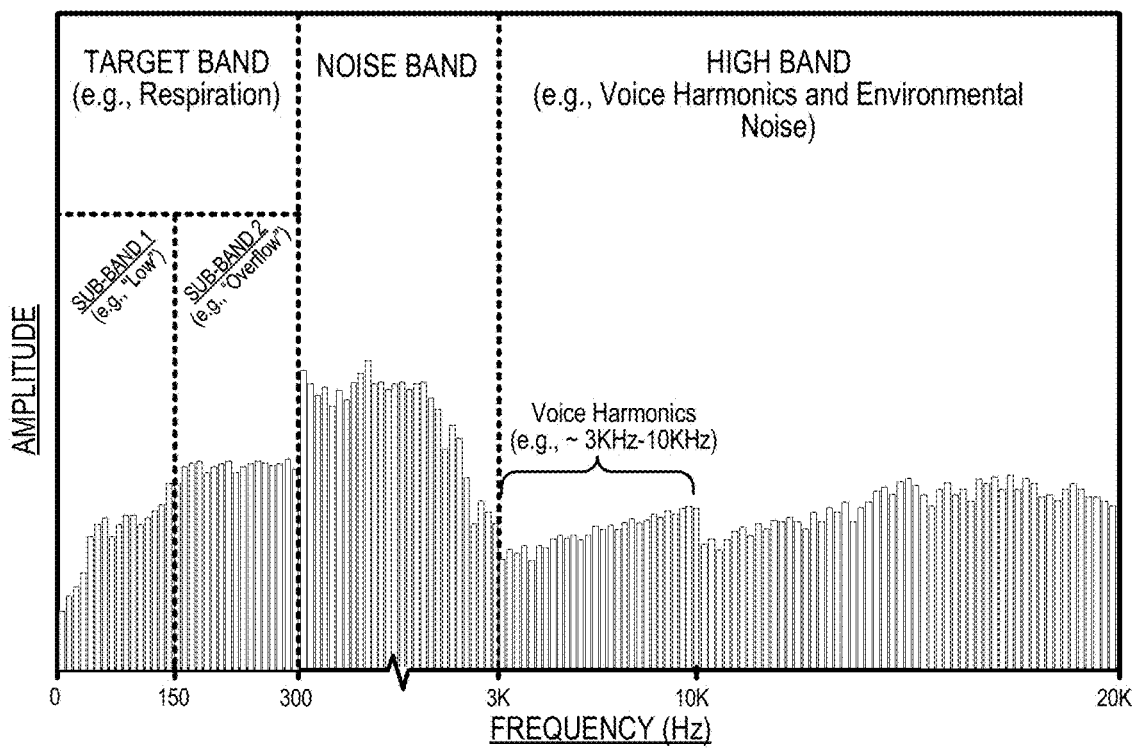
FIG. 8A illustrates a graph of a frequency spectrum of an audio signal received by the exemplary respiration monitoring device shown in FIG. 6.
Figure 8B:
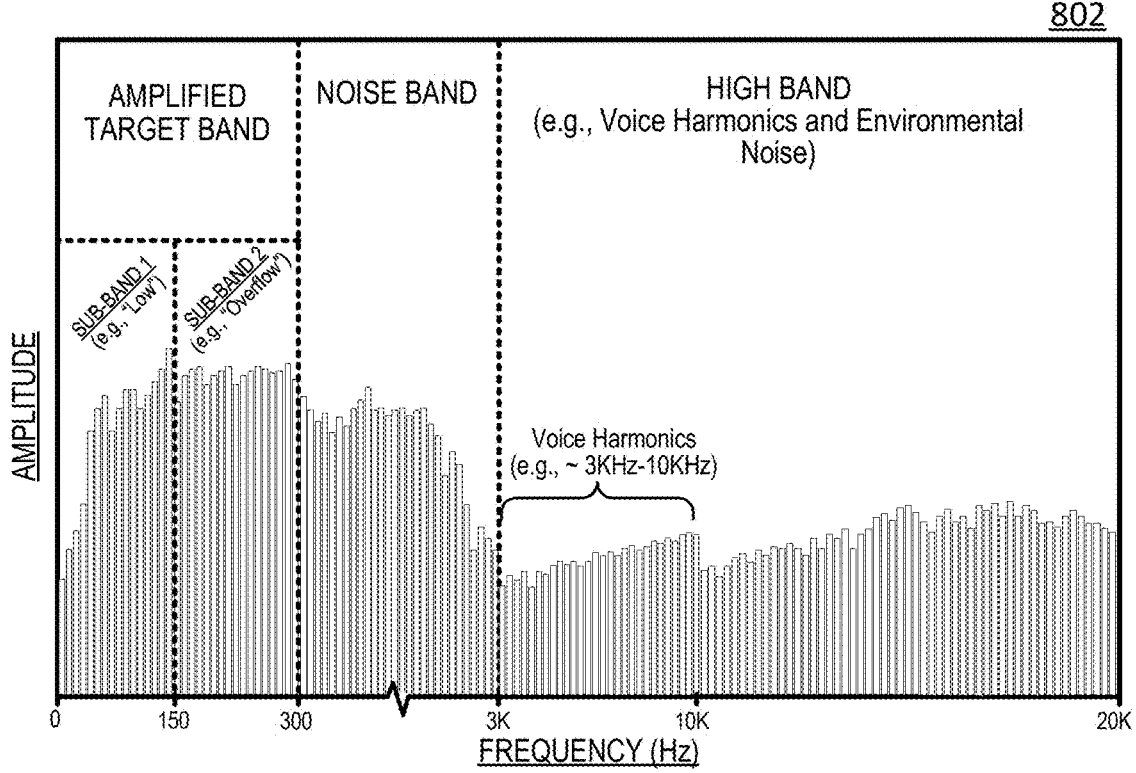
FIG. 8B illustrates a graph of the frequency spectrum shown in FIG. 8A, further showing gains applied to a target frequency band to create an amplified target band.
Figure 8C:
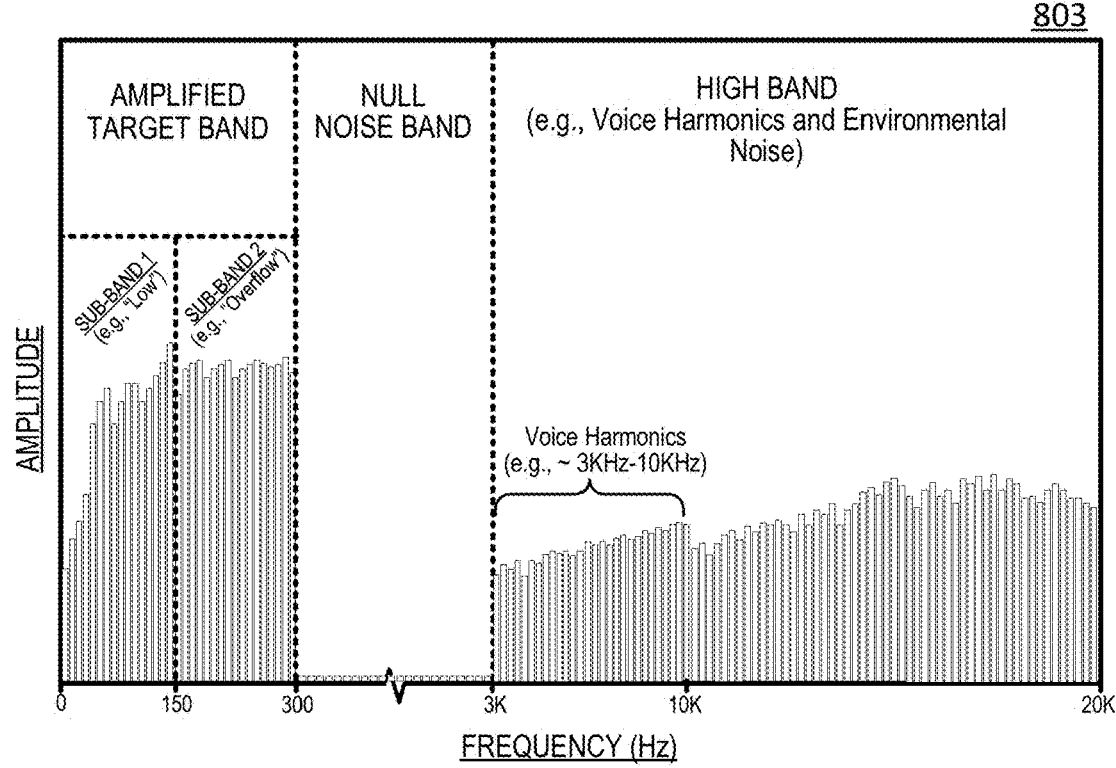
FIG. 8C illustrates a graph of the frequency spectrum shown in FIG. 8B, further showing a filter applied to a noise frequency band to create a null noise band.
Figure 8D:
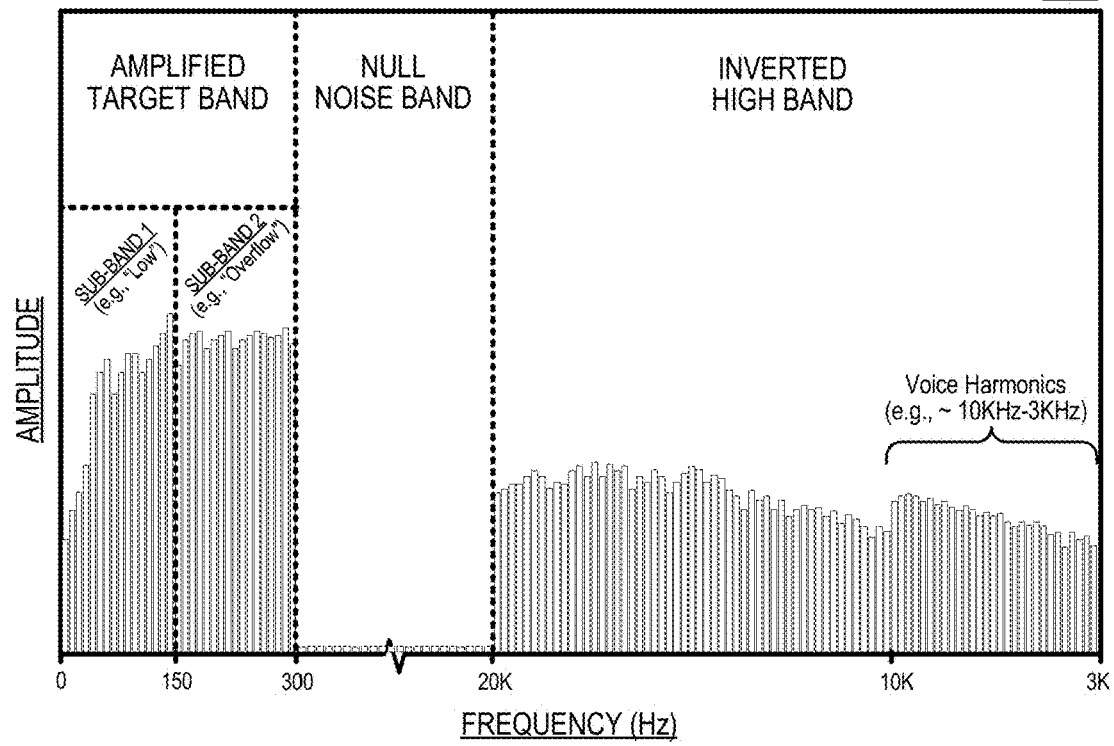
FIG. 8D illustrates a graph of the frequency spectrum shown in FIG. 8C, further showing an inversion procedure applied to a high frequency band to create an inverted high frequency band.
Figure 8E:
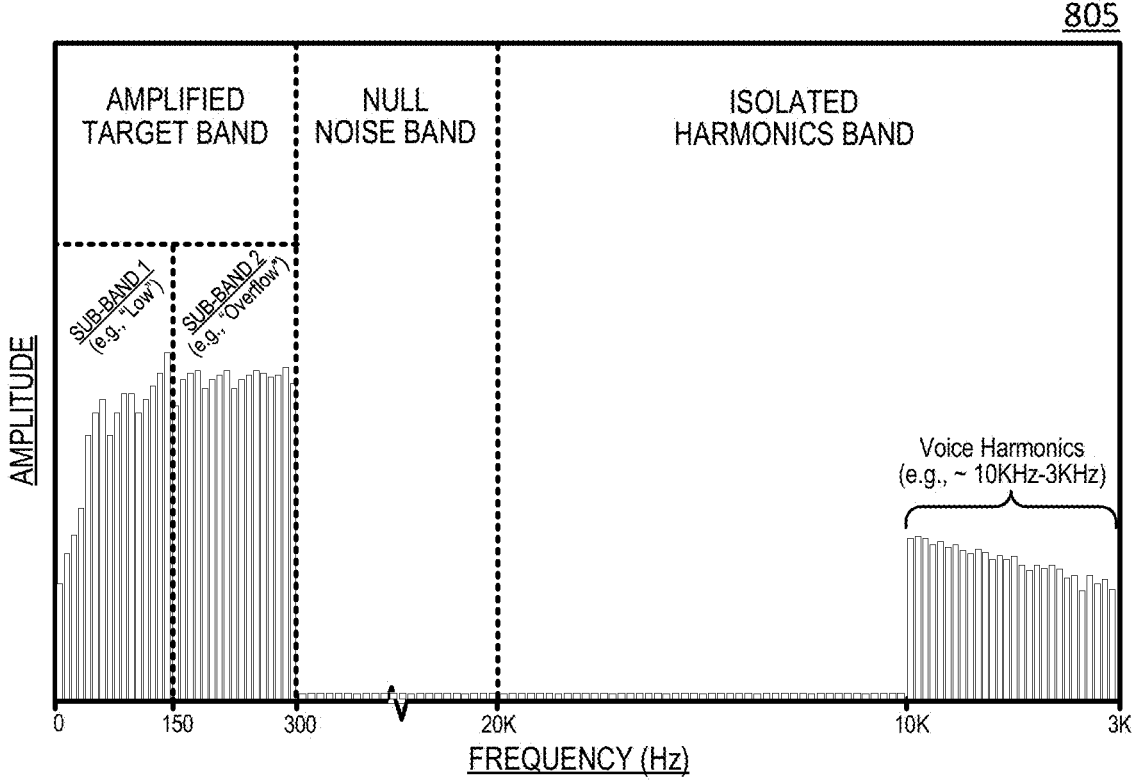
FIG. 8E illustrates a graph of the frequency spectrum shown in FIG. 8D, further showing a filter applied to the inverted high frequency band to create an isolated harmonics frequency band.
Figure 8F:
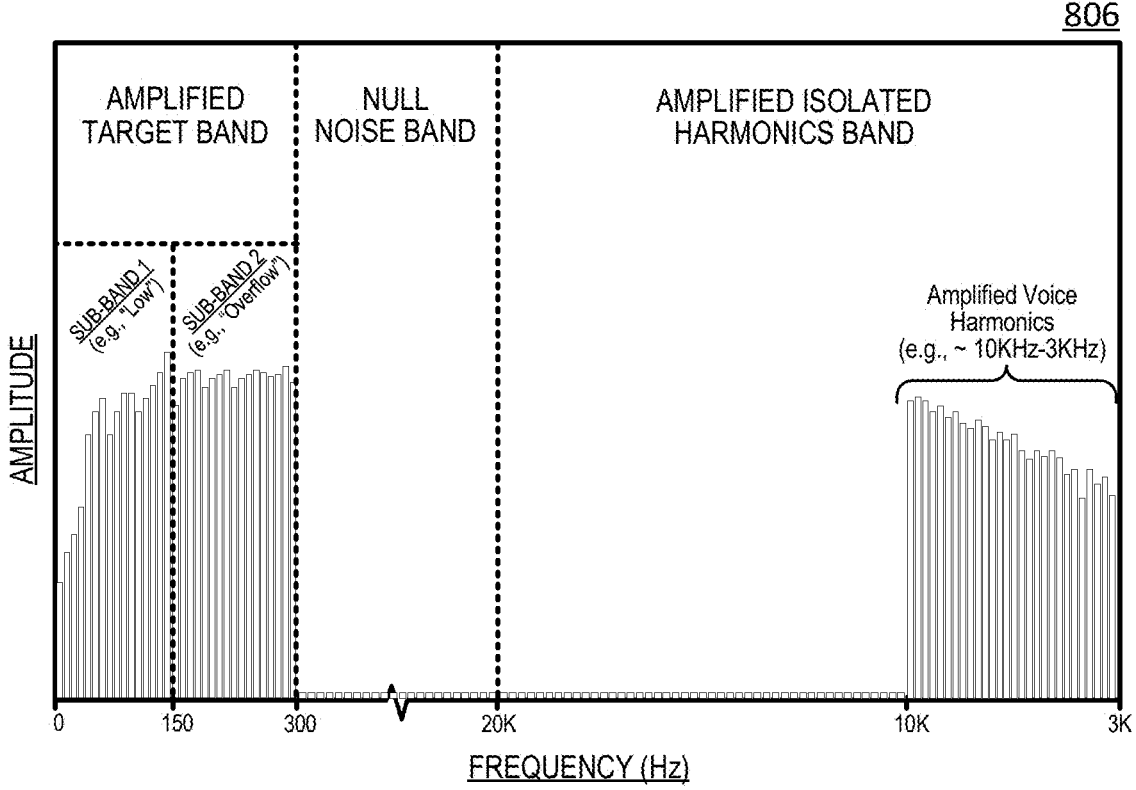
FIG. 8F illustrates a graph of the frequency spectrum shown in FIG. 8E, further showing gains applied to the isolated harmonics frequency band to create an amplified isolated harmonics frequency band.
Figure 8G:
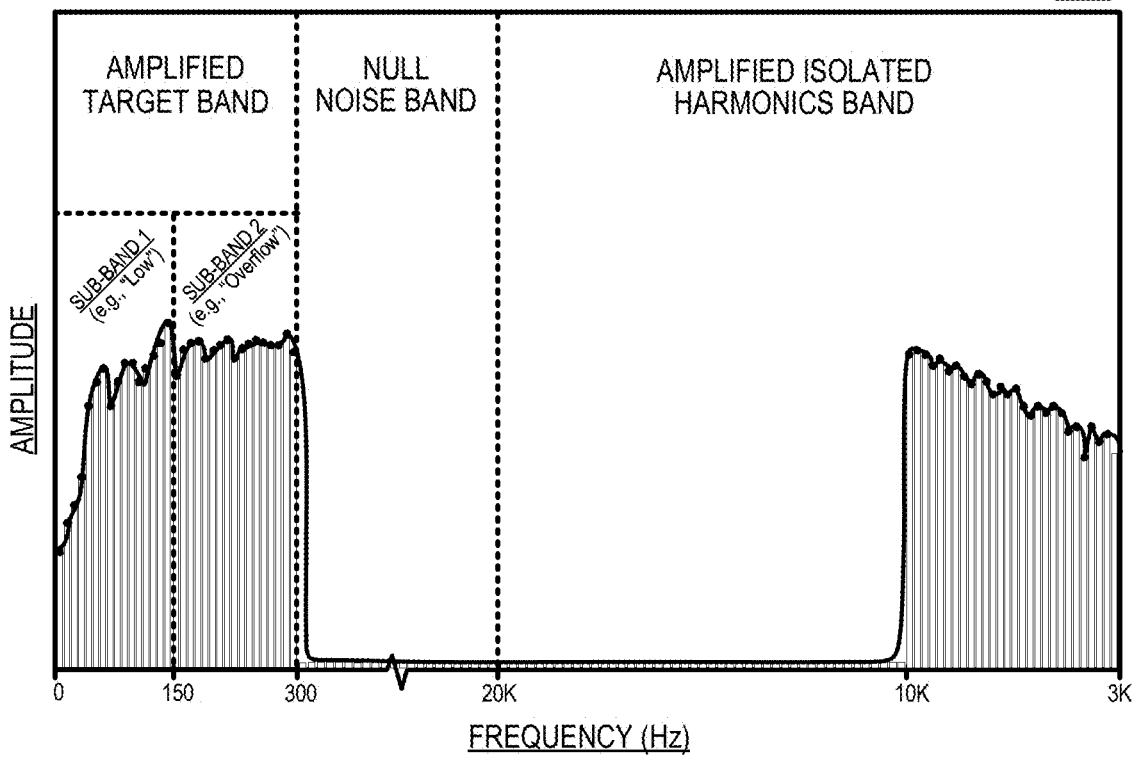
FIG. 8G illustrates a graph of the frequency spectrum shown in FIG. 8E, further showing a plot of the amplitude distributions.
Figure 8H:
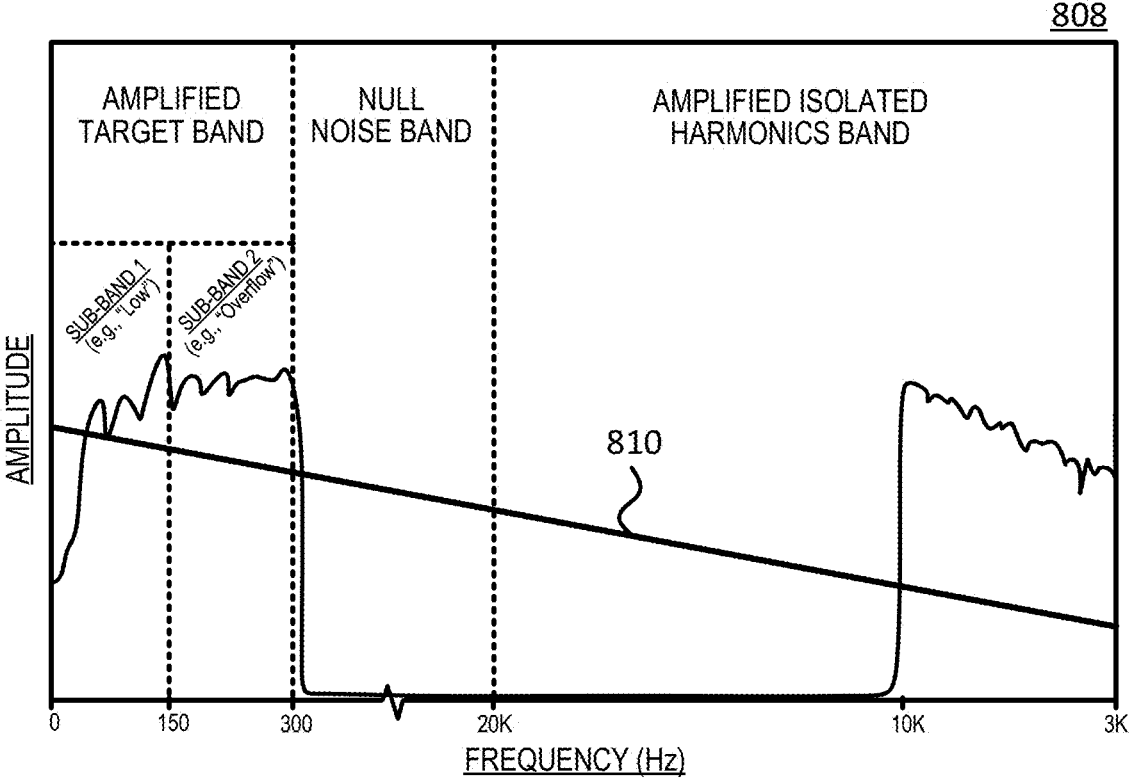
FIG. 8H illustrates the plot of the amplitude distributions shown in FIG. 8G, further showing a mean slope line calculated between the amplitude distributions of frequencies in the amplified target band and the amplified isolated harmonics band, where the slope value of the mean slope line indicates respiration of a user.

Collectively and as a brief overview to discussion of FIGS. 8A-8H, the processing steps of the respiration monitoring process compare frequency responses associated with respiration with frequency responses associated with voice harmonics in order to distinguish between an exhalation and speech (and/or or other environmental sounds). The respiration monitoring process shown in these figures generally includes converting audio data into a frequency spectrum and identifying a "target" frequency band associated with respiration (FIG. 8A), amplifying the amplitudes in the target frequency band to create an amplified target frequency band (FIG. 8B), filtering unwanted noise from a "noise" frequency band (FIG. 8C), inverting the amplitude responses in a "high" frequency band associated with certain voice harmonics and environmental noise (FIG. 8D), filtering the inverted high frequency band to create an isolated harmonics frequency band (FIG. 8E), amplifying the isolated harmonics frequency band to create an amplified isolated harmonics frequency band (FIG. 8F), and determining an average or mean slope value for the resultant frequency spectrum to determine whether the audio data corresponds to an exhalation (FIGS. 8G and 8H).

In detail, referring to FIG. 8A, graph 801 shows an initial frequency spectrum or a distribution of amplitudes of a respective frequencies represented by an audio signal or audio data.

As discussed above, a device such as headset 104, receives the audio data by its input component or an input component 203. Input component 203 includes electronic interfaces such as voice coils, diaphragms, drivers, and other components such as those found in microphones and speakers. In operation, input component 203 converts analog sounds or noises into digital data or audio data. Curved baffle 114 facilitates accurately receiving and converting audio signals into audio data by creating a partially confined space for directing sound from a user 102 toward a desired focal point—here, input component 203 when frame 112 is coupled or attached to headset 104.

In graph 801, the respiration monitoring process applies a Fourier Transform (e.g., ref. FIG. 7) to the audio data to transform the audio data into its constituent distribution of frequency amplitudes. The Fourier Transform can include a DTFT, and FFT, and/or any other type of transform that converts time-based audio signals into frequency-based amplitudes.

Once converted, the respiration monitoring process further identifies several frequency bands. Here, the frequency bands include a "target" frequency band, a "noise" frequency band, and a "high" frequency band. The target frequency band, also referred to as a first frequency band, includes a first set of frequencies associated with respiration. The noise frequency band, also referred to as a second frequency band, includes a second set of frequencies associated with unwanted sounds or noise. The high frequency band, also referred to as a third frequency band, includes a third set of frequencies associated with voice. The respiration monitoring process generally categorizes or assigns different frequencies to the above mentioned frequency bands for subsequent analysis, filtering, and comparison, in order to ultimately determine whether or not the audio data represents a user's exhalation or voice/speech. In general, the human ear can hear up to 20 kHz and human speaking voice ranges from approximately 100 Hz to 6 KHz. In this broad range, most of the energy is concentrated at fundamental voice frequencies that occur below 500 Hz. However, it should also be noted that the energy for consonant sounds occurs over 1 kHz. Harmonics refers to multiples of a given fundamental frequency and correspond to frequency ranges above a fundamental frequency. For example, if a fundamental frequency of a particular sound is 500 Hz, the harmonic frequencies related to the 500 Hz sound would occur at 1 KHz, 1.5 KHz, and so on, until the energy of the sound is dissipated. In the context of voice or speech, the harmonics at higher frequencies help distinguish one sound from the next and thus, help render the speech intelligible. As discussed, the respiration monitoring process filters and isolates frequency responses corresponding to respiration in the target frequency band from frequency responses corresponding to voice in the high frequency band, which specifically corresponds to harmonic frequencies.

As shown, the first set of frequencies in the target frequency band includes frequencies from approximately 0 Hz-300 Hz. The first frequency band may be determined based on various calibration parameters, which can include frequencies derived from specific user inputs (to determine frequency responses for unique breathing patterns), derived iteratively from multiple user(s) inputs (to determine average frequency responses for general respiration), derived from machine learning or neural networks (e.g., based on training data), and/or combinations thereof.

As an example, the respiration monitoring process can be calibrated to identify specific frequencies corresponding to respiration (e.g., the target frequency band) based on users performing specific breathing/voice exercises during a setup or calibration procedure where frequencies associated with respiration or breathe may be identified and isolated from other frequencies based on a frequency amplitude responses. In this example, a user could perform a breathing exercise in a quiet space (e.g., without additional environmental noise such as voice). The resultant frequency response of the user's respiration in this quiet space could be associated with the target frequency band. Similarly, the user could perform voice or speech exercises and the resultant frequency response could be associated with the high frequency band.

In addition, the calibration parameters may be adjusted and customized based on other factors, including the type of device, the specific input interface (e.g., sensitivity of the microphone), placement or position of the input interface, the curvature of a baffle (e.g., curved baffle 114), and so on. Importantly, however, the target frequency band includes specific frequencies associated with user respiration (e.g., exhalation and/or inhalation).

The respiration monitoring process also accounts for potential overlap between respiration frequencies and one or more fundamental frequencies associated with voice or speech. Here, the respiration monitoring process segments the target frequency band into one or more "sub-target" bands, illustrated as "sub-target band 1" and "sub-target band 2." Sub-target band 1 includes "low" frequencies (e.g., approximately 0 Hz-150 Hz) that are primarily associated with only respiration, while sub-target band 2 includes "overflow" frequencies (e.g., approximately 150 Hz-300 Hz) that can be associated with respiration and/or lower fundamental frequencies associated with voice. In this fashion, sub-target band 2 can include frequencies from both respiration as well as lower portions of fundamental voice frequencies.

Notably, the respiration monitoring process may also segment the target frequency band into sub-target frequency bands for subsequent processing operations, where individual "gains" are applied to each respective sub-target frequency band in order to more granularly amplify specific portions of the respiration related frequencies. For example, there may be more certainty that the sub-target band 1 is primarily (and/or only) associated respiration frequencies, and thus, sub-target band 1 may be assigned a different (e.g., higher) gain than sub-target band 2. Conversely, sub-target band 2 may include respiration related frequencies and portions of fundamental voice frequencies, and thus may be assigned a lower gain than sub-target band 1.

With respect to the remaining frequency bands shown in graph 801, the respiration monitoring process also identifies an unwanted "noise" frequency band and a "high" frequency band. The "noise" frequency band generally includes frequencies associated with the other portions of fundamental voice frequencies such as mid/high voice frequencies at approximately 300 Hz-3K Hz. The "high" frequency band generally includes frequencies associated with higher order voice harmonics at approximately 3K Hz-20K Hz. As mentioned, it is appreciated that the exact frequencies associated with the noise frequency band and/or the high frequency band may be calibrated and/or adjusted based on inputs from one or more users, hardware considerations, neural networks/machine learning, and the like.

FIG. 8B illustrates a graph 802 that shows the respiration monitoring process applying specific gains to the target frequency band, resulting in an "amplified" target frequency band. As mentioned, the respiration monitoring process can apply one or more gains or multipliers to target frequency band, which can include individual gains applied to each sub-target band 1 and the sub-target band 2. These gains amplify or exaggerate the amplitudes of the target frequency band, which thereby amplifies the amplitudes of frequencies associated with respiration. As discussed below, the respiration monitoring process ultimately distinguishes between respiration (e.g., exhalation) and certain higher order voice harmonics based a comparison between the amplitudes for respiration frequencies in the target frequency band and the higher order voice harmonics in the high frequency band. Amplifying or exaggerating to the amplitudes improve the accuracy of the ultimate respiration determination FIG. 8C provides graph 803 that shows the respiration monitoring process filtering the noise frequency band to create a "null" noise frequency band. The noise frequency band includes frequency responses for unwanted or undesired "noise," which in this context, corresponds to portions of fundamental voice frequencies and portions of first order harmonics from approximately 300 Hz-3K Hz. The null noise band may be created by, for example, applying a multiplier of zero to the constituent frequencies in the noise frequency band, and/or applying a band-stop filter to the frequency spectrum to reduce the amplitudes of the frequencies in the second frequency band to zero.

The unwanted frequencies in the null noise band can negatively impact the respiration (e.g., exhalation) determination. For example, the unwanted frequency responses may include fundamental noise and/or environmental noise that does not relate or correspond to any respiration frequency. In turn, keeping such frequency responses can skew an average slope line between the target frequency band and the high frequency band (which corresponds to voice harmonics). As discussed below, the average slope line is used to detect respiration (e.g., exhalation) for a user and distinguish respiration from voice/speech. In this fashion, the processing step represented by graph 803 reduces or otherwise eliminates the irrelevant noise corresponding to mid/high fundamental voice frequencies.

FIG. 8D provides graph 803 that shows the respiration monitoring process inverting or reversing the high or third frequency band, which creates an inverted high frequency band. As shown, the frequency responses associated with relevant voice harmonics occur between approximately 3K Hz-10K Hz. As mentioned, fundamental voice frequencies generally fall between approximately 100 Hz and 500 Hz. Higher-frequency voice harmonics add depth, clarity, and color to human speech, and are present at multiples of respective fundamental frequencies. However, as discussed, the energies or amplitudes for voice harmonics dissipate at higher multiples of its fundamental frequency. Thus, the relevant harmonic frequencies corresponding to human voice will be represented by higher energies or amplitudes closer 3K Hz than 10K Hz.

Reversing or inverting these harmonic amplitudes will reverse a resultant slope line for the same. For example, a slope line for the reversed harmonic amplitudes may be negative if voice harmonics are not present or positive if voice harmonics are present. However, the slope line and/or the slope value of the reversed harmonic amplitudes only reflect the presence (or absence) of voice frequency responses. Accordingly, as discussed with respect to FIG. 8H (below), the disclosed respiration monitoring techniques evaluate the slope line in the context of the entire frequency spectrum, which compares the slope value over the amplified target frequency band, the nulled noise spectrum (which will have a slope value of 0), and the inverted high frequency band, in order to detect the presence or absence of exhalation.

Put differently, reversing or inverting the frequency responses in the high frequency band increases the accuracy of determining whether or not respiration—e.g., here, an exhalation—is present in the audio data. For example, just as the local slope line for the reversed harmonic amplitudes (e.g., 3K Hz-10K Hz) may be negative is the voice harmonics are not present or positive if the voice harmonics are present, the global slope line over the entire frequency spectrum (which includes the amplified target frequency band) (e.g., approximately 0 Hz-20K Hz) will be have a negative trend if the frequency responses corresponding to respiration are greater than the frequency responses corresponding to voice. Conversely, the global slope line over the frequency spectrum will have a positive trend if the frequency responses corresponding to respiration are smaller or less than the frequency responses corresponding to voice. Thus, inverting the frequency amplitude distributions for the reversed harmonic amplitudes reverses its corresponding local slope line, which in turn, reinforces the global positive or negative slope trends thereby increasing the accuracy of detecting whether or not the audio data corresponds to respiration. For example, referring to graphs 803 (FIG. 8C) and 804 (FIG. 8D), the amplitudes of frequencies in the high frequency band shown in graph 803 have a generally positive or rising slope line, while the amplitudes of frequencies in the inverted high frequency band shown in graph 804 are reversed or inverted and have a generally negative or falling slope line.

FIGS. 8E and 8F illustrate graphs 805 and 806, respectively. In graph 805, the respiration monitoring process filters the relevant harmonic frequencies associated with voice (e.g., approximately 3K Hz-10K Hz) by nulling frequencies from approximately 20K Hz-10K Hz. This creates the illustrated isolated harmonics frequency band. It is appreciated that the same filtering techniques discussed above with respect to the null noise frequency band in FIG. 8C (graph 803) may be used to filter and isolate the relevant harmonic frequencies associated with voice in graph 805. In graph 806, the respiration monitoring process applies a gain to the voice relevant harmonic frequencies to create the illustrated amplified isolated harmonics band.

FIGS. 8G and 8H illustrate graphs 807 and 808, respectively. In graph 807, the respiration monitoring process plots a line through the amplitudes of the frequencies over the frequency spectrum, and in graph 808, the respiration monitoring process determines a slope line 810 for the amplitudes of frequencies over the frequency spectrum.

As shown in FIG. 8H, the respiration monitoring process determines slope line 810 over the frequency spectrum (e.g., approximately 0 Hz-20K Hz). As is appreciated by those skilled in the art, slope line 810 may represent a mean or an average of amplitude distributions over the frequency spectrum. In some embodiments, the mean or average slope line may represent a moving average and/or a weighted moving average. Additionally, smoothing factors may also be applied to determine slope line 810, where increasing frequencies are associated with decreasing weights (or vice versa), as appropriate.

A slope value associated with slope line 810 can be calculated as a simple derivative function. Importantly, the respiration monitoring process determines whether or not the frequency spectrum corresponds to an exhalation based on the slope value. Here, the underlying value of slope line 810 is compared to a threshold value to determine whether respiration is present in the audio data. The threshold value is determined based on a variety of factors, which include unique specifications of the device 600 (e.g., microphone sensitive, microphone placement, curvature of the curved baffle, and so on) as well as user-specific considerations (e.g., unique user breathing patterns, etc.). Accordingly, the threshold value may be adjusted or calibrated for specific users or for specific equipment.

In the specific context of graph 808, the respiration monitoring process compares the average or mean slope value corresponding to slope line 810 to the threshold value. A slope value less than the threshold value represents an exhalation, while a slope value greater than the threshold value does not represent an exhalation. In other words, the respiration monitoring process detects an exhalation when the frequency response corresponding to amplified target band (e.g., respiration) is greater than or exceeds the frequency response corresponding to the amplified isolated harmonics frequency band (e.g., voice).

In some embodiments, the respiration monitoring process iteratively analyzes audio data over different time periods to determine a respiration rate of a user. For example, the respiration monitoring process may evaluate and compare exhalations present in audio data for different time periods. In these examples, the respiration monitoring process may further compare time stamps corresponding to the different time periods to determine a respiration rate of the user. In other embodiments, the respiration monitoring process may also determine exhalation intensity based on the amplitudes of the amplified target band. Accordingly, the respiration monitoring process may use temporal or spectral analyses to determine respiration rates and/or intensities, and further provide biofeedback to a user pertaining to the same.

FIGS. 8A-8E illustrate various aspects of the disclosed respiration monitoring process. Collectively, FIGS. 8A-8E show steps to determine a frequency spectrum for audio data, identify and filter specific frequency bands within the frequency spectrum, determine a slope line for the frequency spectrum, and determine whether the frequency spectrum indicates the presence or absence of respiration (e.g., exhalation) based on a slope value of the slope line. Although the respiration monitoring process has been discussed with respect to determining an exhalation, the same or a substantially similar process may be employed to determine an inhalation. For example, it is appreciated that to determine an inhalation, the gains applied to the respective target band and the isolated harmonics band may be different since inhalations frequencies are typically associated with a smaller frequency response amplitudes.

Figure 9A:
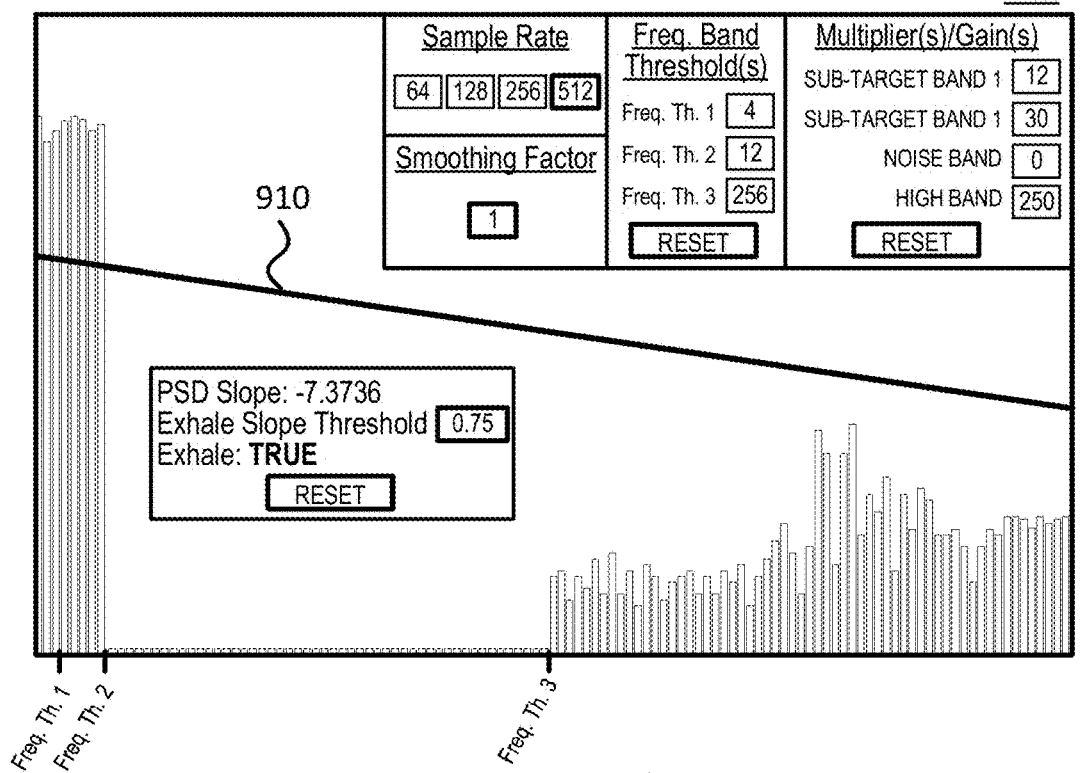
FIG. 9A illustrates a Graphical User Interface (GUI) for modifying and applying the disclosed respiration monitoring techniques to audio signals detected by an input component on a wearable headset.
Figure 9B:
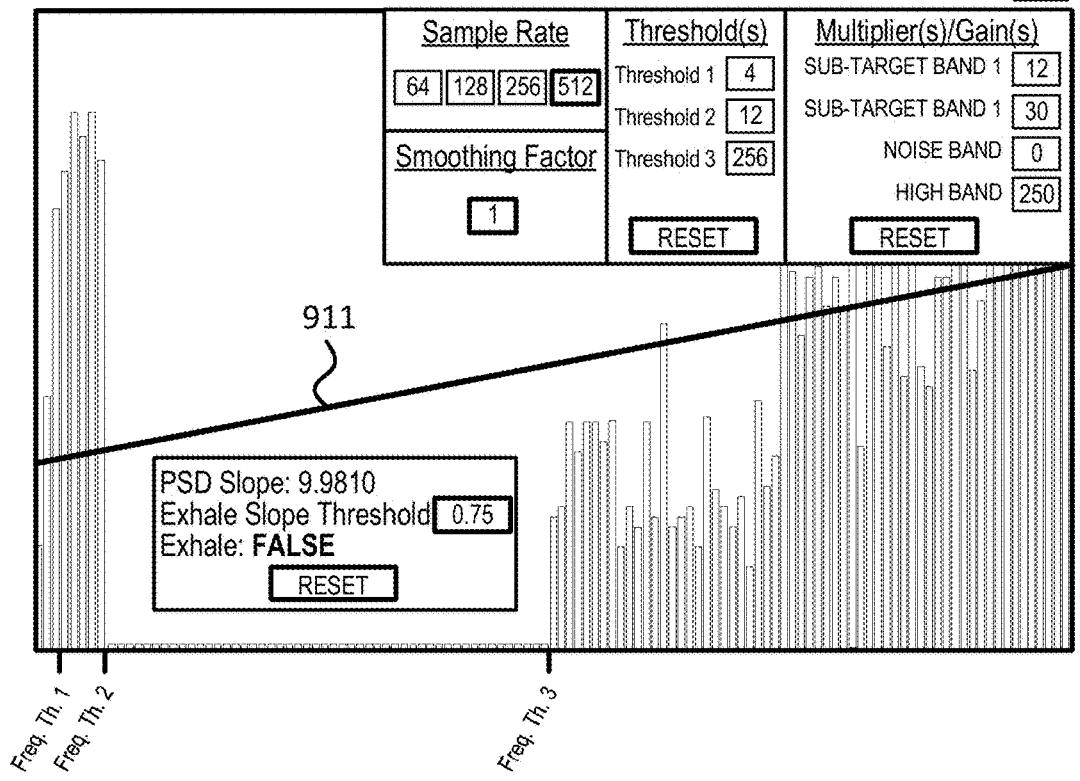
FIG. 9B illustrates another Graphical User Interface (GUI) for modifying and applying the disclosed respiration monitoring techniques to audio signals detected by an input component on a wearable headset.

FIGS. 9A and 9B illustrate respective Graphical User Interfaces (GUIs) 901 and 902, which present tools for executing and adjusting the above-discussed respiration monitoring process. As illustrated, GUI 901 shows a declining slope line 910 that indicates an exhalation is present in the audio data, and GUI 902 shows an increasing slope line 911 that indicates an exhalation is not present in the audio data. These indications are shown as Boolean values, where true corresponds to a detected exhalation, and false corresponds to no detected exhalation.

GUIs 901 and 902 include various input elements that allow an administrator or a user to choose a sampling rate, a smoothing factor, frequency band thresholds, filtering options, multipliers or gains, and a slope threshold value. Other possible GUI configurations may further include a time-domain visualization of respiration or a distribution of breathing rates over time, or any other additional information pertaining to respiration that a user or administrator would find useful in determining or modifying a set of customized parameters for the respiration monitoring process.

As discussed, the resultant respiration determination may be represented by a Boolean "true" or "false" designation. A "true" designation represents a scenario where the amplitudes in the amplified first frequency band are, on average, greater than the amplitudes for the inverted third frequency band (and/or the amplified isolated harmonics band), thereby indicating the presence of respiration. A "false" designation represents a scenario where the amplitudes in the inverted third frequency band (and/or the amplified isolated harmonics band) are, on average, greater than the amplitudes in the amplified first frequency band. In this scenario, no exhalation is detected as the harmonic frequencies associated with voice are greater than the frequencies associated with respiration. The distinction of the "false" designation is particularly important, as while a user is talking, some of the frequencies affected by exhalation may still be active; the distinction of weighing the effect of the human voice on the frequency spectrum ensures that respiration is not being reported for when the user is speaking.

Collectively, the slope lines and corresponding slope values shown in FIGS. 8A-8H and 9A-9B demonstrate how negative trends and/or negative slope values correspond(s) to the presence of respiration (e.g., exhalation) in audio data. These negative trends and values represent situations where the frequency amplitudes corresponding to respiration (e.g., the amplified target band) are greater than the frequency amplitudes corresponding to voice harmonics (e.g., the amplified isolated harmonics band). However, it is also appreciated that the positive or negative nature of the slope value may, in some embodiments, may be reversed (e.g., multiplied by −1) to provide an intuitive meaning to the slope value such that a positive slope value corresponds to a positively detected exhalation and a negative slope value corresponds to no detected exhalation. In general, however, the slope value indicates whether or not respiration (exhalation in particular) is present in audio data. In the context of the disclosed respiration monitoring process, the device performing the process (e.g., headset 104, device 600, etc.) further modifies an experience presented to the user based on the detected respiration.

Figure 10:
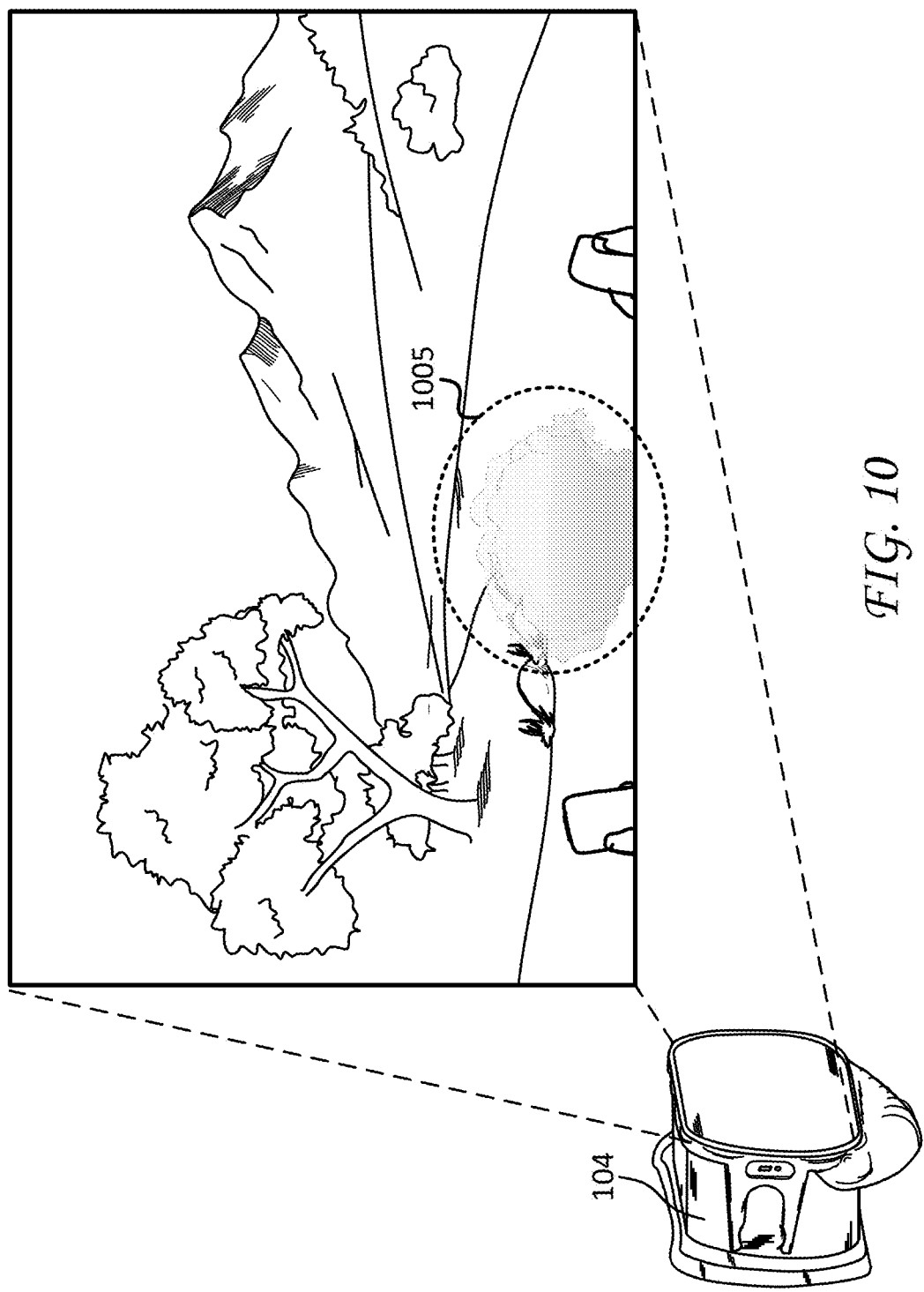
FIG. 10 illustrates a Virtual Reality (VR) environment showing a graphical element corresponds to respiration such as an exhale.

For example, FIG. 10 illustrates a Virtual Reality (VR) environment 1000 presented to a user wearing headset 104. In operation, headset 104 executes the disclosed respiration monitoring process to measure the user's biometrics and more specifically, to detect the user's exhalation. After headset 104 detects the user's exhalation, headset 104 can modify, adjust, or otherwise present biofeedback content to the user, such as in the form of a graphical element 1005.

Graphical element 1005 is a visual representation of the user's exhalation. Graphical element 1005 represents a cloud of condensation reminiscent of breathing outside in cold weather, which may be presented in real-time with the user's exhalations. Graphical element 1005 represents one form of a visual presentation, however, it is appreciated that such visual representation may any form that represents the user's respiration metrics and/or respiration rates. For example, the visual representations can include graphical displays, numbers, rhythmic scenes (e.g. an ocean, a flame, a swing, or some other scene), colorful shapes, and so on. Importantly, the visual representations may be modified based on the user's respiration rate and/or the respiration intensity.

In addition, other types of non-visual content may also be adjusted based on the user's respiration—e.g., increasing/decreasing volumes, changing sounds, providing haptic feedback, and so on. In some embodiments, the respiration monitoring process may modify the content to proactively change the user's state of mind and/or emotions to promote calmness, reduce stress, and the like. For example, the respiration monitoring process may adjust the content to calm the user and relieve acute anxiety or restlessness. In another example, the content can be adjusted to aid meditation by matching, then slowing the presentation of content. In general, modifying the content presented to the user based on the user's respiration allows for a highly customizable experience based on individual breathing patterns.

Figure 11:
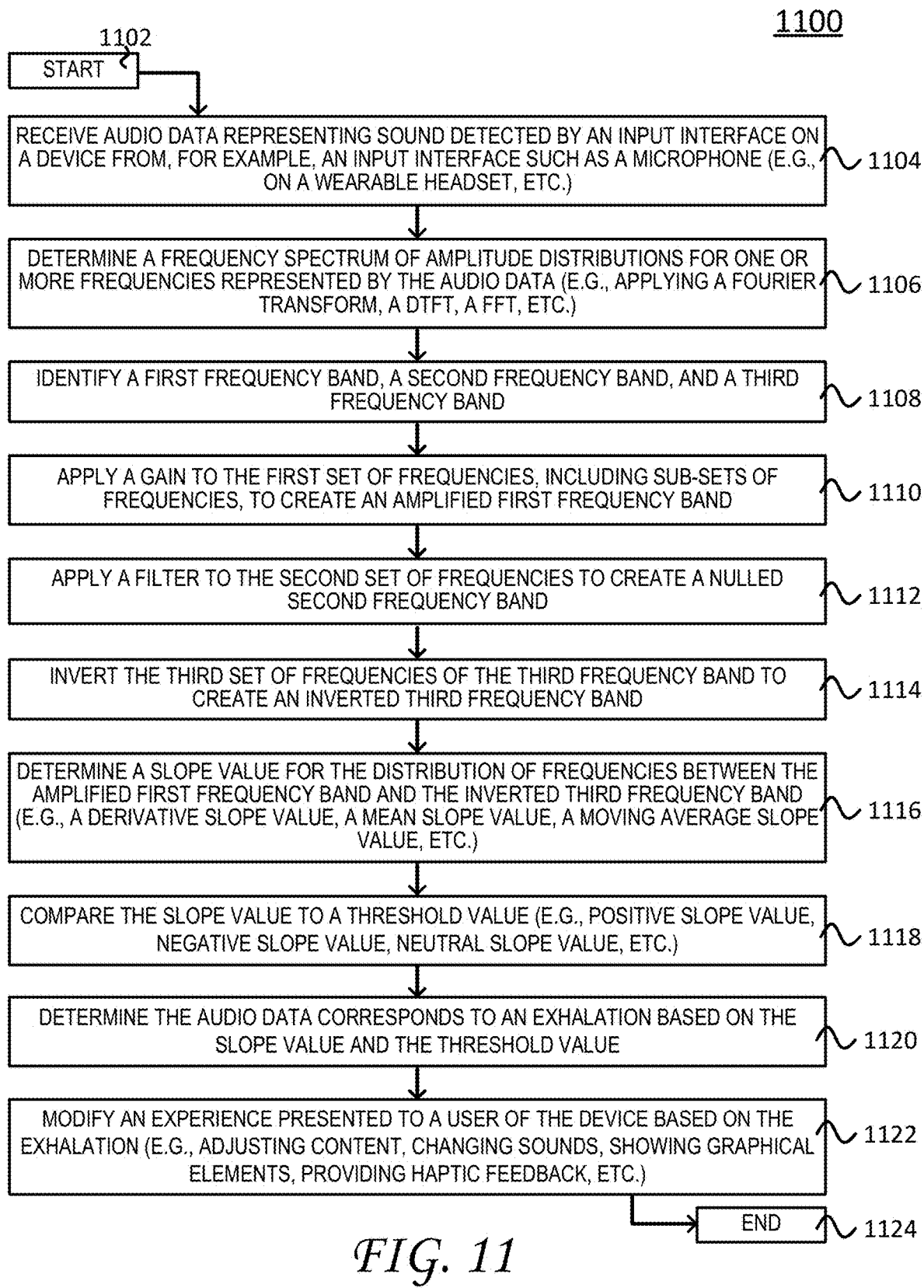
FIG. 11 illustrates a schematic block diagram of a procedure for monitoring respiration according to one or more examples of this disclosure.

FIG. 11 illustrates a schematic block diagram of a procedure 1100 for monitoring respiration according to one or more examples of this disclosure (e.g., respiration monitoring process/services 644). For purposes of discussion herein, procedure 1100 is described in the context of a device such as a headset that is configured to perform this procedure.

Process 1100 begins with step 1102, and continues to step 1104 where, as discussed above, the device receives audio data representing sound detected by an input interface on the device. Notably, the input interface can include electronic interfaces such as voice coils, diaphragms, drivers, and other components such as those found in microphones and speakers. The input interface operably receives analog sound signals and converts those analog signals into digital signals in the form of audio data.

The device determines, in step 1106, a frequency spectrum of amplitude distributions of one or more frequencies represented by the audio data. Here, the device applies a Fourier Transform to the audio data to convert or transform the audio data from a time-based signal into its constituent frequencies.

The device also identifies, in step 1108, a first frequency band including a first set of frequencies associated with respiration, a second frequency band including a second set of frequencies associated with noise, and a third frequency band including a third set of frequencies associated with voice harmonics (e.g., ref. FIG. 8A). Notably, in some embodiments, the device further identifies sub-sets of the first frequency band (e.g., the target frequency band), which can include a low sub-band corresponding to respiration frequencies and an overflow sub-band corresponding to respiration frequencies and portions of low fundamental voice frequencies.

Next, in step 1110, the device further applies a gain to the first set of frequencies to create an amplified first frequency band in step 1110 (e.g., ref. FIG. 8B). In some embodiments, individual gains may be applied to the sub-bands of the first frequency band.

In step 1112, the device applies a filter to the second set of frequencies to create a nulled second frequency band (e.g., ref. FIG. 8C), and in step 1114, the device inverts the third set of frequencies of the third frequency band to create an inverted third frequency band (e.g., ref. FIG. 8D). In some embodiments, the device may optionally apply a second filter to portions of the third frequency band to isolate certain higher order voice harmonics (e.g., ref. FIG. 8E). Additionally, in these embodiments, the device may also apply a gain to the isolated voice harmonics to create an amplified isolated harmonics frequency band (e.g., ref. FIG. 8F).

The device further determines, in step 1116, a slope value for the frequency spectrum, which includes the amplitude distributions of the amplified first frequency band and at least a portion of the inverted third frequency band (e.g., the amplified isolated harmonics frequency band). As discussed, the slope value corresponds to a slope line for the amplitude distributions over the filtered and inverted frequency spectrum. This slope line may represent a moving average and/or a weighted moving average. In some embodiments, the device can apply one or more smoothing factors to the slope line.

The device further compares the slope value to a threshold value in step 1118. As discussed above, the slope value and/or the threshold value can correspond to a positive number or a negative number. The device then determines, in step 1120, that the audio data corresponds to respiration, specifically exhalation, based on the comparison between the slope value to the threshold value. In some embodiments, exhalation is detected when the slope value is less than the threshold value since a negative trend indicates the frequency response corresponding to respiration (e.g., the first frequency band) is greater than the frequency response corresponding to voice (e.g., the inverted third frequency band and/or the amplified isolated harmonics frequency band). However, as mentioned above, the slope value may be reversed (e.g., multiplied by −1) to provide an intuitive meaning to the slope value such that a positive slope value greater than the threshold avlue corresponds to a positively detected exhalation.

The device further modifies an experience presented to the user in step 1122 based on the detected exhalation. The detected exhalation is a form of biometric information that can be leveraged to inform a user about his or her respiration rate. As shown in FIG. 10, the exhalation may be visually or audibly represented and/or the exhalation may be represented in a form of haptic feedback to the user. In some embodiments, the device may proactively leverage the detected exhalation to control of influence the user's state of mind or emotions.

Procedure 1100 subsequently ends at step 1124, but may return again to step 1104, where the wearable headset receives audio signals and convert the audio signals into audio data. It should be noted that certain steps within procedure 1100 may be optional, and further, the steps shown in FIG. 11 are merely example steps for illustration— additional steps may be included or excluded as desired. Further, while a particular order of the steps is shown, this ordering is merely illustrative, and any suitable arrangement of the steps may be utilized without departing from the scope of the embodiments herein. For example, while the procedure shown in FIG. 11 illustrates a procedure for monitoring respiration based on one set of received audio data, it is appreciated that procedure 1100 can be executed as part of an iterative process to determine respiration of a user over a given time period. More specifically, procedure 1100 shows a determination of a single exhalation based on the received audio data, however, this procedure may be continuously run on any suitable device, wearable headset, and the like, to determine exhalations of a user over time. It is further appreciated that further analysis may be done on these exhalations to determine respiration rates.

The techniques described herein provide for monitoring biometric information for a user, typically in conjunction with a wearable headset (e.g., a VR headset). These techniques particularly monitor the user's respiration and detect exhalations in audio data, and modify an experience presented to the user based on the same. Thus, the respiration monitoring process described herein provides accurate and efficient solutions to providing biofeedback to the user based on audio data.

While there have been shown and described illustrative embodiments to determine latency distributions amongst pairs of network nodes, network topology mapping, and the like, it is to be understood that various other adaptations and modifications may be made within the spirit and scope of the embodiments herein. For example, the embodiments have been shown and described herein using response times in factors of a generic time (t), however it is appreciated that latency or response times may be measured in specific fractions, or portions of seconds (e.g., milliseconds, microseconds, etc.) or other appropriate measures of time.

While there have been shown and described illustrative embodiments of the respiration monitoring process, it is to be understood that various other adaptations and modifications may be made within the spirit and the scope of the embodiments herein. For example, the embodiments have been shown and described herein calculating a slope value using a derivative of the distribution of frequencies between the amplified first frequency band and the inverted third frequency band, wherein an average value of the derivative is used to determine the slope value. However, it is appreciated that a slope value may be found using a variety of techniques including but not limited to applying smoothing factors, taking a slope based on peak-to-valley measurements between the first amplified frequency band and the inverted third frequency band, or by considering a moving average of the derivative or the frequency spectrum.

The foregoing description has been directed to specific embodiments. It will be apparent, however, that other variations and modifications may be made to the described embodiments, with the attainment of some or all of their advantages. For instance, it is expressly contemplated that the components and/or elements described herein can be implemented as software being stored on a tangible (non-transitory) computer-readable medium, devices, and memories (e.g., disks/CDs/RAM/EEPROM/etc.) having program instructions executing on a computer, hardware, firmware, or a combination thereof. Further, methods describing the various functions and techniques described herein can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on. In addition, devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example. Instructions, media for conveying such instructions, computing resources for executing them, and other structures for supporting such computing resources are means for providing the functions described in these disclosures. Accordingly this description is to be taken only by way of example and not to otherwise limit the scope of the embodiments herein. Therefore, it is the object of the appended claims to cover all such variations and modifications as come within the true spirit and scope of the embodiments herein.

The invention claimed is:

1. A method for monitoring respiration, the method comprising:
   receiving, by a processor, audio data representing sound detected by an input interface on a device;
   determining, by the processor, a frequency spectrum of amplitude distributions for one or more frequencies represented by the audio data;
   identifying, by the processor, a first frequency band, a second frequency band, and a third frequency band from the frequency spectrum of amplitude distributions, the first frequency band including a first set of frequencies associated with respiration, the second frequency band including a second set of frequencies associated with noise, and the third frequency band including a third set of frequencies associated with voice harmonics;
   applying, by the processor, a gain to the first set of frequencies to create an amplified first frequency band;
   applying, by the processor, a filter to the second set of frequencies to create a nulled second frequency band;
   inverting, by the processor, the third set of frequencies of the third frequency band to create an inverted third frequency band;
   determining the frequency spectrum corresponds to an exhalation based on a slope value between amplitude distributions of the amplified first frequency band and amplitude distributions of at least a portion of the inverted third frequency band; and
   modifying an experience presented to a user of the device based on the exhalation.

2. The method of claim 1, further comprising:
   applying a second filter to the inverted third frequency band to create an isolated harmonics band;

applying a second gain to the isolated harmonics band to create an amplified isolated harmonics band; and wherein determining the frequency spectrum corresponds to the exhalation further comprises determining the frequency spectrum corresponds to the exhalation based on the slope value between the amplitude distributions of the amplified first frequency band and amplitude distributions of the amplified isolated harmonics band.

3. The method of claim 1, wherein determining the frequency spectrum corresponds to the exhalation further comprises determining the slope value for the amplitude distributions based on a moving average of the amplitude distributions.

4. The method of claim 1, wherein determining the frequency spectrum corresponds to the exhalation further comprises:
determining the frequency spectrum corresponds to the exhalation based on one of a positive slope value or a negative slope value.

5. The method of claim 1, wherein determining the frequency spectrum corresponds to the exhalation, further comprises:
determining the frequency spectrum corresponds to the exhalation when the slope value exceeds a threshold value.

6. The method of claim 1, wherein determining the frequency spectrum of amplitude distributions for the one or more frequencies represented by the audio data further comprises:
calculating, by the processor, at least one of a Discrete Time Fourier Transform (DTFT) or a Fast Fourier Transform (FFT) for the audio data to determine the frequency spectrum of amplitude distributions.

7. The method of claim 1, wherein the frequency spectrum of amplitude distributions for the one or more frequencies represented by the audio data, further comprises:
applying a Fourier transform to the audio data to determine the frequency spectrum of amplitude distributions.

8. The method of claim 1, wherein the first frequency band has at least two subsets of frequencies that include at least a target-subset of frequencies and an overflow subset of frequencies, and
wherein applying the gain to the first set of frequencies comprises applying a first gain to the target-subset of frequencies, and
applying a second gain to the overflow subset of frequencies.

9. The method of claim 1, wherein the input interface on the device includes a microphone, the method further comprising:
converting sound from an environment proximate to the device into the audio data using the microphone.

10. The method of claim 1, wherein applying the filter to the second set of frequencies further comprises, applying a band pass filter to the frequency spectrum to null the second set of frequencies.

11. The method of claim 1, wherein modifying the experience presented to the user of the device further comprises adjusting content presented to the user.

12. The method of claim 1, wherein the device includes at least one of a wearable headset, an Augmented Reality (AR) headset, an Enhanced Reality (ER) headset, or a Virtual Reality (VR) headset.

13. The method of claim 1, further comprising:
determining the frequency spectrum corresponds to an exhalation for a time period; and
determining a rate of respiration based on the time period.

14. A device for monitoring respiration, the device comprising: one or more input interfaces;
a processor coupled to the input interfaces and adapted to execute one or more processes; and
a memory operable to store instructions executable by the processor, wherein the instructions, when executed by the processor, are operable to:
receive audio data representing sound detected by an input interface on a device;
determine a frequency spectrum of amplitude distributions for one or more frequencies represented by the audio data;
identify a first frequency band, a second frequency band, and a third frequency band from the frequency spectrum of amplitude distributions, the first frequency band including a first set of frequencies associated with respiration, the second frequency band including a second set of frequencies associated with noise, and the third frequency band including a third set of frequencies associated with voice harmonics;
apply a gain to the first set of frequencies to create an amplified first frequency band;
apply a filter to the second set of frequencies to create a nulled second frequency band;
invert the third set of frequencies of the third frequency band to create an inverted third frequency band;
determine the frequency spectrum corresponds to an exhalation based on a slope value between amplitude distributions of the amplified first frequency band and at least a portion of amplitude distributions of the inverted third frequency band; and
modify an experience presented to a user of the device based on the exhalation.

15. The device of claim 14, wherein the instructions, when executed by the processor, are further operable to:
apply a second filter to the inverted third frequency band to create an isolated harmonics band;
apply a second gain to the isolated harmonics band to create an amplified isolated harmonics band; and
wherein the instructions to determine the frequency spectrum corresponds to the exhalation are further operable to determine the frequency spectrum corresponds to the exhalation based on the slope value between the amplitude distributions of the amplified first frequency band and amplitude distributions of the amplified isolated harmonics band.

16. The device of claim 14, wherein the instructions to determine the frequency spectrum corresponds to the exhalation are further operable to determine the slope value between the amplitude distributions based on a moving average of the amplitude distributions.

17. The device of claim 14, wherein the instructions to determine the frequency spectrum corresponds to the exhalation are further operable to:
determine the frequency spectrum corresponds to the exhalation when the slope value exceeds a threshold value.

18. A tangible, non-transitory, computer-readable media having instructions encoded thereon, the instructions, when executed by a processor, are operable to:
receive audio data representing sound detected by an input interface on a device;

determine a frequency spectrum of amplitude distributions for one or more frequencies represented by the audio data;

identify a first frequency band, a second frequency band, and a third frequency band from the frequency spectrum of amplitude distributions, the first frequency band including a first set of frequencies associated with respiration, the second frequency band including a second set of frequencies associated with noise, and the third frequency band including a third set of frequencies associated with voice harmonics;

apply a gain to the first set of frequencies to create an amplified first frequency band;

apply a filter to the second set of frequencies to create a nulled second frequency band;

invert the third set of frequencies of the third frequency band to create an inverted third frequency band;

determine the frequency spectrum corresponds to an exhalation based on a slope value between amplitude distributions of the amplified first frequency band and at least a portion of amplitude distributions of the inverted third frequency band; and modify an experience presented to a user of the device based on the exhalation.

19. The tangible, non-transitory, computer-readable media of claim 18, wherein the instructions, when executed by the processor, are further operable to:

apply a second filter to the inverted third frequency band to create an isolated harmonics band;

apply a second gain to the isolated harmonics band to create an amplified isolated harmonics band; and wherein the instructions to determine the frequency spectrum corresponds to the exhalation are further operable to determine the frequency spectrum corresponds to the exhalation based on the slope value between the amplitude distributions of the amplified first frequency band and the amplified isolated harmonics band.

20. The tangible, non-transitory, computer-readable media of claim 18, wherein the instructions to determine the frequency spectrum corresponds to the exhalation are further operable to:

determine the frequency spectrum corresponds to the exhalation when the slope value exceeds a threshold value.

\* \* \* \* \*